US012629343B2

(12) United States Patent
Xie et al.

(10) Patent No.: US 12,629,343 B2
(45) Date of Patent: May 19, 2026

(54) MULTI-LAYER TRANSDERMAL DRUG DELIVERY SYSTEM CONTAINING IBUPROFEN OR STRUCTURAL ANALOGUE THEREOF

(71) Applicant: Demotech, Inc., Beijing (CN)

(72) Inventors: Wenwei Xie, Beijing (CN); Song Lu, Beijing (CN); Shuangjiang He, Beijing (CN); Nan Chen, Beijing (CN)

(73) Assignee: Demotech, Inc., Beijing (CN)

( * ) Notice: Subject to any disclaimer, the term of this patent is extended or adjusted under 35 U.S.C. 154(b) by 782 days.

(21) Appl. No.: 17/292,387

(22) PCT Filed: Oct. 29, 2019

(86) PCT No.: PCT/CN2019/113909
§ 371 (c)(1),
(2) Date: May 7, 2021

(87) PCT Pub. No.: WO2020/093906
PCT Pub. Date: May 14, 2020

(65) Prior Publication Data
US 2022/0008351 A1 Jan. 13, 2022

(30) Foreign Application Priority Data
Nov. 9, 2018 (CN) ........................ 201811332928.4

(51) Int. Cl.
*A61K 9/70* (2006.01)
*A61K 31/192* (2006.01)
*A61K 47/02* (2006.01)

(52) U.S. Cl.
CPC .......... *A61K 9/7023* (2013.01); *A61K 9/7084* (2013.01); *A61K 31/192* (2013.01); *A61K 47/02* (2013.01)

(58) Field of Classification Search
CPC .. A61K 9/7023; A61K 9/7084; A61K 9/7061; A61K 9/7069; A61K 9/7046;
(Continued)

(56) References Cited

U.S. PATENT DOCUMENTS 10,966,936 B2 * 4/2021 Lee ........................ A61K 41/00
2005/0032900 A1 2/2005 Krauser
(Continued)

FOREIGN PATENT DOCUMENTS

CN 1162260 A 10/1997
CN 1387842 A 1/2003
(Continued)

OTHER PUBLICATIONS

European Communication pursuant to Article 94(3) EPC for European Application No. 19881630, dated Jan. 26, 2023, 11 pages.
(Continued)

*Primary Examiner* — Rebecca E Eisenberg
*Assistant Examiner* — Timothy L Flynn
(74) *Attorney, Agent, or Firm* — TraskBritt

(57) ABSTRACT

A multi-layer transdermal drug delivery system containing ibuprofen or a structural analogue thereof, comprising a transdermal patch containing ibuprofen or a structural analogue thereof and a second combined layer. The transdermal patch comprises a polymer matrix layer, the polymer matrix layer comprising an active ingredient, a compound containing at least one amino group, and a pressure-sensitive adhesive. All or some of active ingredient-amino compound salts or all or some of free active ingredients formed in the polymer matrix layer are kept in a uniform dissolution state in the polymer matrix, and can be stably stored before use, without recrystallization. The transdermal drug delivery system can continuously and controllably deliver a therapeutically effective amount of ibuprofen or a structural
(Continued)

analogue thereof for 12 to 24 hours in the absence of a transdermal enhancer, has excellent wearing ability, and avoids a cold flow phenomenon.

20 Claims, 6 Drawing Sheets

(58) Field of Classification Search
CPC ...... A61K 31/192; A61K 47/02; A61K 9/703; A61K 9/7038; A61K 9/7092; A61P 29/00
See application file for complete search history.

(56) References Cited

U.S. PATENT DOCUMENTS

| | | | | |
|---|---|---|---|---|
| 2006/0034904 | A1* | 2/2006 | Weimann | A61M 37/0092 604/20 |
| 2006/0172002 | A1* | 8/2006 | Takada | A61K 9/7053 424/449 |
| 2007/0219171 | A1 | 9/2007 | Lulla et al. | |
| 2007/0259029 | A1* | 11/2007 | McEntire | A61K 8/8152 424/449 |
| 2009/0022987 | A1 | 1/2009 | Hashino et al. | |
| 2009/0062754 | A1 | 3/2009 | Tang | |
| 2009/0161065 | A1 | 6/2009 | Smith, III et al. | |
| 2013/0005816 | A1* | 1/2013 | Chen | A61K 47/22 514/570 |
| 2013/0005817 | A1 | 1/2013 | Tani | |
| 2017/0087098 | A1 | 3/2017 | Ritzdorf et al. | |
| 2018/0163014 | A1* | 6/2018 | Tinkl | C08K 9/04 |
| 2018/0369174 | A1* | 12/2018 | Frangakis | A61K 31/195 |

FOREIGN PATENT DOCUMENTS

| | | | |
|---|---|---|---|
| CN | 1443532 | A | 9/2003 |
| CN | 1582142 | A | 2/2005 |
| CN | 1827094 | A | 9/2006 |
| CN | 1886105 | A | 12/2006 |
| CN | 1897927 | A | 1/2007 |
| CN | 101045041 | A | 10/2007 |
| CN | 101347417 | A | 1/2009 |
| CN | 101437500 | A | 5/2009 |
| CN | 101455654 | A | 6/2009 |
| CN | 101489985 | A | 7/2009 |
| CN | 101502499 | A | 8/2009 |
| CN | 101522178 | A | 9/2009 |
| CN | 101842065 | A | 9/2010 |
| CN | 101961418 | A | 2/2011 |
| CN | 102000043 | A | 4/2011 |
| CN | 102370631 | A | 3/2012 |
| CN | 102630160 | A | 8/2012 |
| CN | 102940618 | A | 2/2013 |
| CN | 102949382 | A | 3/2013 |
| CN | 104825567 | A | 8/2015 |
| CN | 105030864 | A | 11/2015 |
| CN | 105250243 | A | 1/2016 |
| CN | 105520921 | A | 4/2016 |
| CN | 106692114 | A | 5/2017 |
| CN | 106913560 | A | 7/2017 |
| CN | 107441063 | A | 12/2017 |
| CN | 108078961 | A | 5/2018 |
| CN | 109432061 | A | 3/2019 |
| EP | 2094250 | A1 | 9/2009 |
| EP | 2545912 | A1 | 1/2013 |
| JP | 2013-514347 | | 4/2013 |
| JP | 2013-173805 | A | 9/2013 |
| JP | 2016-084308 | A | 5/2016 |
| JP | 2017-105724 | A | 6/2017 |
| JP | 2018-140970 | A | 9/2018 |
| WO | 93/00058 | A1 | 1/1993 |
| WO | 2005/123046 | A1 | 12/2005 |
| WO | 2008/010025 | A1 | 1/2008 |
| WO | 2008/061677 | A1 | 5/2008 |
| WO | 2011/034323 | A2 | 3/2011 |
| WO | 2012/151427 | A1 | 11/2012 |
| WO | 2017/117554 | A1 | 7/2017 |
| WO | 2018/070406 | A1 | 4/2018 |

OTHER PUBLICATIONS

Hui, M., et al., "The effect of ion-pair formation combined with penetration enhancers on the skin permeation of loxoprofen", Drug Deliv., vol. 23, No. 5, 2016, pp. 1550-1557.

Notice of Reasons for Refusal received for Japanese Patent Application No. 2021-525301, mailed on Jul. 11, 2022, 14 pages (7 pages of English Translation and 7 pages of Original Document).

Supplementary European Search Report and Opinion for European Application No. 19881630, dated Aug. 6, 2021, 14 pages.

Berton et al., "Transdermal Bioavailability in Rats of Lidocaine in the Forms of lonic Liquids, Salts, and Deep Eutectic", ACS Med. Chem. Lett., vol. 8, (2017), pp. 498-503.

Chinese Pharmacopoeia, 2015 edition, vol. IV, general principle 0512.

Chinese Pharmacopoeia, 2015 edition, vol. IV, general principle 0931, Fourth method-paddle over disk.

Cilurzo et al., "Polymethacrylates as crystallization inhibitors in monolayer transdermal patches containing ibuprofen", European Journal of Pharmaceutics and Biopharmaceutics, vol. 60, (2005), pp. 61-66.

Comyn, Handbook of Pressure Sensitive Adhesive Technology, Book Review, International Journal of Adhesion & Adhesives, vol. 20, (2000), pp. 427.

Gee et al., "Transdermal Delivery of Ibuprofen Utilizing a Novel Solvent-Free Pressure-sensitive Adhesive (PSA): Tepi® Technology", Journal of Pharmaceutical Sciences, vol. 103, (2014), pp. 909-919.

International Search Report for International Application No. PCT/CN2019/113909, mailed Jan. 23, 2020, 7 pages with English Translation.

International Written Opinion for International Application No. PCT/CN2019/113909, mailed Jan. 23, 2020, 12 pages with English Translation.

Jannat et al., "Formulation and Evaluation of Sustained Release Matrix Type Transdermal Film of Ibuprofen", Bangladesh Pharmaceutical Journal, vol. 15, Issue 1, (2012), pp. 17-21.

Jiang et al., "Ion-pair formation combined with a penetration enhancer as a dual strategy to improve the transdermal delivery of meloxicam", Drug Deliv. and Transl. Res., vol. 8, (2018), pp. 64-72.

Michaelis et al., "Mixture design approach for early stage formulation development of a transdermal delivery system", Drug Dev. Ind. Pharm. Early Online, (2014), pp. 1-9.

Technology of Pressure-Sensitive Adhesives and Process, Istvan Benedek, Mikhail M Feldstein, CRC press, 2009.

Tombs et al., "Transdermal Delivery of Ibuprofen Utilizing a Novel Solvent-Free Pressure-sensitive Adhesive (PSA): Tepi® Technology", Journal of Pharmaceutical Innovation, vol. 13, (2018), pp. 48-57.

Chinese First Office Action for Application No. 202010983262.X dated Jul. 21, 2020, 14 pages with machine translation.

Chinese Second Office Action for Application No. 202010983262.X dated Jul. 28, 2022, 13 pages.

Chinese Third Office Action for Application No. 202010983262.X dated Sep. 28, 2022, 14 pages.

Japanese Decision of Refusal for Application No. 2021-525301 dated Feb. 6, 2023, 17 pages.

Japanese Notice of Refusal for Application No. 2021-525301 dated Jul. 11, 2022, 18 pages.

Japanese Notice of Refusal for Application No. 2021-525301 dated Jul. 12, 2023, 9 pages.

Japanese Notice of Refusal for Application No. 2021-525301 dated Nov. 21, 2022, 9 pages.

European Communication pursuant to Article 94(3) EPC for European Application No. 19881630, dated Jun. 26, 2024, 3 pages.

Chinese Search Report for Chinese Application No. 202010983262, dated Feb. 7, 2022, 1 page.

(56) References Cited

OTHER PUBLICATIONS

European Communication pursuant to Article 94(3) EPC for European Application No. 19881630, dated Jan. 21, 2025, 17 pages.
Michaelis et al., Plasticization and Antiplasticization of an Acrylic Pressure Sensitive Adhesive by Ibuprofen and Their Effect on the Adhesion Properties, European Journal of Pharmaceutics and Biopharmaceutics, (2014), vol. 86, pp. 234-243.

* cited by examiner

MULTI-LAYER TRANSDERMAL DRUG DELIVERY SYSTEM CONTAINING IBUPROFEN OR STRUCTURAL ANALOGUE THEREOF

CROSS REFERENCE

The present application claims priority to Chinese patent application No. 201811332928.4, entitled "Multi-layer transdermal drug delivery system containing ibuprofen or structural analogue thereof", and filed on Nov. 9, 2018, the entire disclosure of which is incorporated herein by reference in its entirety.

TECHNICAL FIELD

The present invention belongs to the technical field of transdermal drug delivery, and specifically relates to a multi-layer transdermal drug delivery system containing ibuprofen or a structural analogue thereof. The system of the present invention contains highly loaded ibuprofen or a structural analogue thereof, and can be uniformly dispersed in a polymer matrix. The system can maintain a continuous and stable delivery of a therapeutically effective dose of ibuprofen or a structural analogue thereof during a period of 12 to 24 hours.

BACKGROUND ART

Ibuprofen is a non-steroidal anti-inflammatory drug (NSAID) used to relieve pain and reduce fever and inflammation. Ibuprofen can non-selectively and reversibly inhibit the activities of cyclooxygenases (COX), COX-1 and COX-2, and COX-1 and COX-2 are the key enzymes for the catalyzed synthesis of prostaglandin (PG) in organisms. By inhibiting the activities of COX-1 and COX-2, the fever and pain symptoms caused by the production of prostaglandin in the body can be reduced or eliminated. Its structural analogues (naproxen, fenoprofen, ketoprofen, flurbiprofen, and loxoprofen) all have similar pharmacological mechanisms and effects.

Since ibuprofen was first marketed in the UK in 1969, there are currently many dosage forms, including oral dosage forms, such as ordinary solid oral tablets, sustained-release capsules, and oral liquids. However, the oral dosage form of ibuprofen has many inconveniences and side effects, such as frequent administration due to short half-life, gastrointestinal irritation, gastrointestinal bleeding and the like. There are also surface preparations of ibuprofen on the market, such as gel creams and suppositories. However, special operations and care are required when using gel creams, which will contaminate clothing and cause local drug loss during use. At the same time, the dosage forms of ibuprofen also include injection, but the injection requires professional operation and is inconvenient to use, and it is only used under special circumstances.

Therefore, there is still a strong demand for the development of other dosage forms of ibuprofen to meet the requirements of convenience of use, rapid onset of action, stable blood drug concentration, and to meet the expectation of one single dose a day. Transdermal drug delivery is an ideal means to meet the requirements of ibuprofen administration.

The modern transdermal drug delivery system (TDDS) mainly refers to the drug delivery method in which the drug in the form of a patch is absorbed viae skin or mucosa and exerts a pharmaceutical effect in the treatment of local parts or the systemic system. The transdermal drug delivery method has many advantages, such as comfort, convenience, long-acting sustained release, no gastrointestinal irritation and no first pass effect, and no invasiveness, and can reduce the fear of taking drugs and the frequency of administration, avoid the fluctuation of blood drug concentration caused by oral absorption, and have higher safety. Transdermal drug delivery has more clinical significance for infants and young children and the elderly who have difficulty in taking drugs. Since the first scopolamine patch (Transderm Scop®) was launched in 1979, people have made a lot of attempts to develop more transdermal drug delivery systems with therapeutic effects. So far, many products have been successfully launched on the market.

According to the combination mode of active ingredients and other auxiliary materials in the patch, the patch can generally be classified into two categories, reservoir systems or drug-in-adhesives. The drug-in-adhesives is obtained by dissolving or dispersing the active ingredients uniformly in a semi-solid composition composed of one or more polymer materials and other pharmaceutically usable auxiliary materials to form a uniform polymer matrix. If the polymer material itself is a pressure-sensitive adhesive, then the polymer material not only plays the role of a drug carrier, but also plays the role of adhering to the skin at the application site. The main factors that need to be considered when designing a drug-in-adhesive polymer matrix patch include the nature of the active ingredient itself and its loading amount, the physical and chemical properties of each component in the polymer matrix, the overall performance of the polymer matrix formed by all components, the external environmental conditions for the production and storage of the patch, the application site and time of the patch, the required drug delivery speed and therapeutic effect, the wearability of the patch and the like.

The polymer matrix patch mainly relies on the passive diffusion of the drug from the matrix into the human body across the skin stratum corneum. Therefore, the main factors determining the diffusion rate are the concentration and saturation degree of the drug in the matrix, and the strength of the interaction between the drug and other components in the matrix, especially the interaction between the polymer and the drug in the composition. Depending on the differences of the nature of the active ingredient and the polymer used, the concentration of the drug in the polymer matrix composition is also different. When the concentration of the active ingredient in the matrix is low and the drug loading amount is small, it is difficult to achieve an ideal drug delivery, especially it is difficult to achieve steady-state delivery. If the drug loading amount is high and reaches or approximates a saturation concentration, the diffusion rate of the drug will be improved accordingly, but the overall adhesive properties of the matrix composition such as adhesion, peel adhesion and shear resistance will be affected or destroyed, and more seriously, the problem of unexpected recrystallization will occur in the active ingredient.

In an attempt to develop a transdermal drug delivery system of ibuprofen, various transdermal drug delivery methods and compositions containing ibuprofen have been publicly reported in the literature. For example, patent applications Nos. CN201410301673.0 and US20090161065A1 respectively disclose an ibuprofen surface composition mainly useing natural polymer xanthan gum to improve the stability of ibuprofen, especially the stability at high temperature, in which the concentration of ibuprofen or its salt is about 5.0%. Patent application No. CN200910079489.5 discloses an ibuprofen transdermal release patch and a preparation method thereof. The drug loading amount of ibuprofen is only between 5% to 15%. Patent application No. CN200710151020.9 discloses an ibuprofen arginine gel, with a preferred active ingredient content of 9.25%. Patent application No. PCT/US2012/036366 discloses an ibuprofen gel with a content of ibuprofen of 15% or less, but a large amount of lower alcohol is used as a solvent, which has potential risks of allergies and volatilization. Patent application No. CN201510759804.4 discloses a long-acting drag-in-adhensive transdermal patch containing ibuprofen and a preparation process thereof, in which a transdermal enhancer is used to achieve continuous release of 12 to 48 hours. Patent application No. CN201510181823.3 discloses a compound ibuprofen patch and a preparation method thereof. Ibuprofen and traditional Chinese medicine compound are used to treat scapulohumeral periarthritis, wherein the content of the active ingredient ibuprofen is about 1%. Patent application No. CN201510379997.0 discloses a pharmaceutical composition containing ibuprofen, in which clove oil (a volatile oil of traditional Chinese medicinal) is used as a transdermal enhancer, wherein the content of the active ingredient ibuprofen is 10% or less, and the dosage form is a gel or cream. A literature (Journal of Pharmaceutical Sciences 103 (2014): 909-919) reported the use of PEG200 and oleic acid as transdermal enhancers, and the transdermal absorption effect of 5% ibuprofen was comparatively investigated. A literature (Drug Dev Ind Pharm, 2014, Early Online: 1-9) reported the idea of designing a patch containing ibuprofen according to ICH Q8, in which only the simple situations using colloid and oleyl alcohol are set, although the content of ibuprofen is up to 20%, but ibuprofen is easy to crystallize and the patch has no practical significance. A literature (European Journal of Pharmaceutics and Biopharmaceutics 60 (2005) 61-66) reported the study on stability of ibuprofen with a content of 3% in the presence of auxiliary materials: propylene glycol, polyethylene glycol, hydrogenated castor oil EL and polymer Eudragit E, RL. A literature (Bangladesh Pharmaceutical Journal 15(1) (2012), 17-21) reported that the drug loading amount of ibuprofen was 5% to 8%, and two polymers, Kollidon SR and Eudragut L, were used as solubilizers. A literature (Journal of Pharmaceutical Innovation 13 (2018), 48-57) only reported that patented colloids were used to develop ibuprofen patches for treating pain.

However, the contents of ibuprofen disclosed in the above documents are relatively low. In order to achieve the delivery of a pharmacologically significant dose within 12 to 24 hours of administration, it is necessary to continue to increase the drug loading amount and saturation concentration in the ibuprofen patch, so as to increase the thermodynamic activity of the active ingredient in the polymer matrix. A suitable balance needs to be found in the aspects of drug loading capacity, saturation, stability, wearability such as the size of the patch, the colloidal properties and the like. However, in the case of high drug loading, the stability of ibuprofen in the patch is a challenge, and there is a risk of recrystallization during storage. But on the other hand, ibuprofen itself is a low-melting phenylpropionic acid derivative, and has both a hydrogen bond acceptor and a hydrogen bond donor. These properties lead to an interaction with the polymer matrix composition, resulting in hindered fluidity in the polymer matrix, which in turn affects the overall transdermal penetration rate of ibuprofen. In addition, the tackifying property of ibuprofen will change the overall colloidal properties of the polymer matrix, such as the patch residues on the skin caused by reduced cohesion, the formation of dark circles around the patch caused by the cold flow problem during use, and the change of property during storage.

SUMMARY OF THE INVENTION

In response to the above problems, the present invention provides a multi-layer transdermal drug delivery system containing ibuprofen or a structural analogue thereof. The system has a high drug loading and a high transdermal penetration efficiency, while being able to continuously and stably maintain a blood drug concentration that can achieve the therapeutic effect for at least 12 to 24 hours. Meanwhile, the system of the present invention can inhibit the crystallization of ibuprofen or its structural analogue under high drug loading, and keep the skin penetration efficiency unchanged during the long-term storage period. Meanwhile, the system of the present invention has good adhesive properties and meets the wearing requirements of the patch during the use.

The following technical and scientific terms involved in the present invention, unless otherwise specified in the context of the present invention, have the same meaning to a person skilled in the art as follows.

Transdermal drug delivery: a method of administration in which the active ingredients enter the local or systemic system through the skin or mucosa.

Transdermal drug delivery system: a system for transdermal drug delivery containing active ingredients, which generally comprises a backing layer, a release film, and a drug delivery layer located between the backing layer and the release film. According to the combination mode of active ingredients and other components in the drug delivery layer, the system can generally be classified into two categories, a reservoir type and a drug-in-adhesive type. The transdermal drug delivery system is also called a patch, and both can be used interchangeably in the present invention.

Composition: different components in the polymer matrix, including but not limited to active ingredients, transdermal enhancers, antioxidants, plasticizers, fillers, and pressure-sensitive adhesives and the like, are physically mixed, and there is no chemical interaction or cross-linking effect between the components.

Compound: different polymers are cross-linked together through chemical action to form stable polymers.

Diffusion: the drug passes through the skin or mucosa passively. The driving force is the difference in the concentration of active ingredients on both sides of the skin, which is directly related to the concentration gradient inside and outside the skin.

Polymer matrix: a polymer matrix refers to a non-water-soluble material in the transdermal drug delivery system, the non-water-soluble material comprises any polymer material combination in which the active ingredient ibuprofen has been added, and also comprises other pharmaceutically acceptable components, such as polyacrylic acid polymer, polysilicone polymer and rubber such as polyisobutylene. Ibuprofen is uniformly dissolved in the polymer matrix of the present invention. The polymer matrix generally comprises a pressure-sensitive adhesive. The polymer matrix is used as the drug delivery layer of the transdermal drug delivery system to form a drug-in-adhesive transdermal drug delivery system.

Pressure-sensitive adhesive: a pressure-sensitive adhesive refers to a type of viscoelastic polymer material. When it is in contact with the surface of most other materials, it can adhere to the material by pressing it with a very light force and can maintain long-term adhesion. There are two types of pressure-sensitive adhesives, one type is a pressure-sensitive adhesive itself, and the other type is one that can achieve the function of a pressure-sensitive adhesive by adding a tackifier or a plasticizer thereto. The pressure-sensitive adhesive has satisfactory physical properties at room temperature, such as good skin adhesion, can maintain adhesion for a certain period of time, and can be peeled off without damaging the skin. Generally, the pressure-sensitive adhesives include acrylic pressure-sensitive adhesives, polysilicone pressure-sensitive adhesives and rubber pressure-sensitive adhesives.

Backing layer: the transdermal drug delivery system generally comprises a backing layer that is impermeable to drugs. One side of the backing layer is directly connected to the polymer matrix layer. The backing layer protects the matrix layer from contacting the surrounding environment when in use, thereby preventing the loss of drugs. The material of the backing layer generally comprises polyester, polyethylene polyvinyl acetate composite film, polyvinyl chloride, polyurethane, metal foil, non-woven fabric and the like. The thickness is generally 2 to 1,000 μm, such as ScotchPak™ 1109 from 3M Company or Cotran™ 9720 from 3M Company.

Release film: it is also called a protective layer. In the present invention, the release film and the protective layer have the same meaning and can be used interchangeably. The transdermal drug delivery system generally comprises a release film, which is directly connected to the other side of the polymer matrix layer, such as ScotchPak™ 9744 from 3M Company. Before the patch is used, the release film needs to be removed.

Single-layer transdermal drug delivery system: it refers to the transdermal drug delivery system in which only one layer of drug-containing polymer matrix is included between the backing layer and the release film, and the polymer matrix contains a polymer pressure-sensitive adhesive. The matrix layer not only plays the role of drug loading, but also plays the role of direct adhesion to the skin.

Therapeutic effective dose: when a patch is in use, the active substance is able to be delivered in a quantity sufficient to achieve the required amount for local or systemic onset of action, thereby achieving a specific pharmacological effect such as cure, alleviation or control of a disease or symptom.

Peel adhesion is the force used to remove the patch from the skin, reflecting the comfort level and whether the patient feels pain.

Adhesion reflects the acting force between the pressure-sensitive adhesive and the skin at the application site, which determines whether the patch will fall off during wearing.

Cohesion reflects the interaction force inside the polymer matrix. Too small cohesion will cause the polymer matrix to exhibit cobwebbing and residue phenomena at the application site.

Shear resistance reflects the degree of slippage of the patch on the skin surface at the application site. For softer parts of the skin, greater shear resistance is required.

Generally, a patch needs to balance the properties of colloidal adhesion, cohesion, peel adhesion, shear resistance and the like. For a medical patch, sufficient cohesion is required so that there will be no residues after the adhesive tape is removed. The increase of the shear force of the colloid will lead to the decrease of adhesion and peel adhesion. Since the balance of the different properties of the pressure-sensitive adhesive mentioned above is actually mutually dependent, it is very difficult to merely improve the cohesion or adhesion without affecting other properties, or without destroying the performance of the overall adhesive system of the pressure-sensitive adhesive. For a pressure-sensitive adhesive, in addition to the four properties mentioned above, it also needs to achieve its own appropriate transparency and oxidation resistance.

Tackifying effect: after a substance is added to the polymer matrix containing a pressure-sensitive adhesive in the transdermal drug delivery system, the fluidity and viscosity of the polymer matrix increases, thereby changing the overall performance of the pressure-sensitive adhesive. Ibuprofen has a tackifying effect after being added to the polymer matrix.

Transdermal enhancer: a substance that can accelerate the diffusion of active ingredients in the polymer matrix into the skin. Generally, it can be miscible with the polymer matrix and evenly dispersed in the polymer matrix.

Cold flow: it means that the adhesion of the polymer matrix layer is greater than the cohesion, resulting in viscoelastic creep, which leads to the instability and unsafety of the patch system. During the wearing, black circles will occur to the patient, and stickness to the protective layer and the packaging container may occur during the storage process.

Active Ingredient Ibuprofen or a Structural Analogue Thereof:

The chemical name of ibuprofen is 2-(4-isobutylphenyl) propionic acid, with a molecular formula of $C_{13}H_{18}O_2$, a molecular weight of 206.3, and a melting point of 74.5° C. to 77.5° C. It is a white crystalline powder, and its chemical structure is as follows:

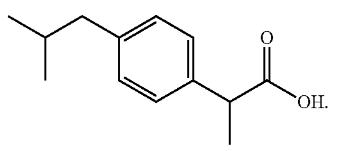

Ibuprofen is a chiral drug with two optical isomers of R and S. Although in vitro studies have shown that only the S isomer has the effect of inhibiting prostaglandin synthesis, the other R isomer with no activity in vitro can be mostly transformed into the S isomer in vivo. Therefore, ibuprofen used in the present invention may be the R or S isomer, a mixture thereof, or a racemate of ibuprofen. Since ibuprofen itself has a carboxyl group, ibuprofen is both a hydrogen bond donor and a hydrogen bond acceptor, and thus, it can be expected that ibuprofen will interact with related components in the polymer matrix. In addition, since ibuprofen itself is relatively weak in efficacy, in order to achieve a therapeutically effective blood drug concentration, a larger dose needs to be delivered. Therefore, a higher drug load is required for the transdermal drug delivery system. However, due to the limitation of its own properties, the solubility of ibuprofen in general patch polymer matrix, especially in the pressure-sensitive polymer matrix system, is relatively low, and ibuprofen is prone to have a high risk of recrystallization, which affects the preservation and use of the patch. One purpose of the present invention is to provide a transdermal drug delivery system in which a sufficient amount of ibuprofen is loaded and dispersed uniformly in a polymer matrix without recrystallization during long-term storage.

The compounds in the following table are similar in structure to ibuprofen, have properties and functions similar to ibuprofen, and can also achieve the purpose of the present invention.

| No. | English name | Chinese Name | Structural formula | General oral dose range/mg |
|---|---|---|---|---|
| 1 | Naproxen | 萘普生 | 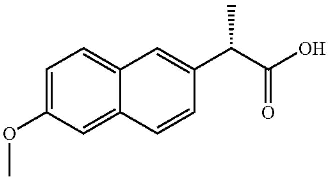 [SMILES: COc1ccc2cc([C@H](C)C(=O)O)ccc2c1] | 500~1000 |
| 2 | Fenoprofen | 非诺洛芬 | 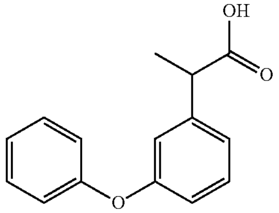 [SMILES: CC(C(=O)O)c1cccc(Oc2ccccc2)c1] | >1000 |
| 3 | Ketoprofen | 酮洛芬 | 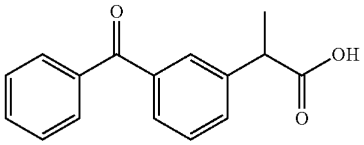 [SMILES: CC(C(=O)O)c1cccc(C(=O)c2ccccc2)c1] | >200 |
| 4 | Flurbiprofen | 氟比洛芬 | 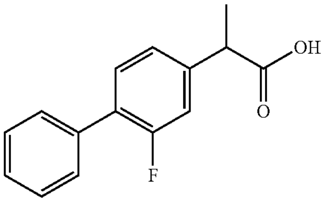 [SMILES: CC(C(=O)O)c1ccc(-c2ccccc2)c(F)c1] | 200~300 |
| 5 | Loxoprofen | 洛索洛芬 | 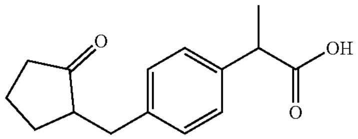 [SMILES: CC(C(=O)O)c1ccc(CC2CCCC2=O)cc1] | 100~200 |

Amino Compounds:

Without relation to any theory, the carboxyl group of ibuprofen or its structural analogue leads to interactions between ibuprofen and the polymer matrix component, which affect its diffusion rate in the polymer matrix. Meanwhile, it also interacts with the skin, especially the cuticle, which affects the diffusion of ibuprofen or its structural analogue into the body. The overall effect causes the diffusion rate of ibuprofen or its structural analogue to be hindered, and an effective therapeutic dose of ibuprofen or its structural analogue cannot be delivered within a given time of use. It is generally believed that neutral molecules, whether they are neutral in themselves or adjusted to neutral by other means, such as the method of acid/base salt formation, can reduce the interaction of the active ingredient with the polymer matrix and the cuticle, so as to achieve the purpose of increasing the passive diffusion rate of the active ingredient. One literature (ACS Med. Chem. Lett. (2017), 8: 498-503 and Drug Deliv. and Transl. Res. (2018) 8:64-72) reported that the concept of salt formation by counter ions, and the transdermal diffusion ability of polar compounds can be increased by the interaction of counter ions. However, there is no good theoretical support for the screening of the counter ions and the degree of change of diffusion ability, and a lot of experimental screening and verification are still needed.

Through a large number of experiments, the present invention surprisingly found that the addition of a compound containing at least one amino group can continuously and controllably maintain stable release of ibuprofen over a given time range of use. Without relation to any theory, the flow of ibuprofen partially salted with the amino compound in the polymer matrix increases, and the interaction with the skin surface is weakened. The salt formation of ibuprofen with the amino compound is reversible. When there is a concentration gradient on the skin surface, the ibuprofen-amino salt at a high concentration releases ibuprofen, which enters the cuticle through diffusion, and then enters the circulatory system. The diffusion rate is related to the concentration of the ibuprofen-amino compound salt. It can be expected that by controlling the content and molar ratio of ibuprofen and the amino compound, a continuous and controllable administration can be established within the expected time range of use, and a therapeutically effective blood drug concentration can be achieved.

The present invention further surprisingly found that after the active ingredient ibuprofen and the compound containing at least one amino group form a salt (that is, an ibuprofen-amino compound salt is formed), the melting point of the salt is greatly lower than that of free ibuprofen, and it is even in a liquid state at room temperature, so that ibuprofen can be evenly dispersed in the polymer matrix and will not recrystallize during long-term storage. On the other hand, the present invention found that the drug loading amount of the polymer matrix to ibuprofen and the saturation degree of ibuprofen can be regulated in a relatively large range, so as to meet the requirements of high-dose administration of ibuprofen.

Based on the above research, the present invention first provides a transdermal patch containing ibuprofen or a structural analogue thereof, and the patch comprising a backing layer, a protective layer, and a polymer matrix layer located between the backing layer and the protective layer. The polymer matrix layer comprises an active ingredient, a compound containing at least one amino group, and a pressure-sensitive adhesive. The active ingredient is ibuprofen or a structural analogue thereof. The structural analogue of ibuprofen is any one or more selected from Naproxen, Fenoprofen, Ketoprofen, Flurbiprofen and Loxoprofen.

Further, in the polymer matrix layer, all or part of the active ingredients form a salt with the compound containing at least one amino group. All or part of the formed active ingredient-amino compound salt (i.e., ibuprofen-amino compound salt, or ibuprofen structural analogue-amino compound salt) and all or part of the free active ingredients remain uniformly dissolved in the polymer matrix, and can be stored stably without recrystallization before use.

Further, the melting point of the formed active ingredient-amino compound salt is lower than the melting point of ibuprofen or its corresponding structural analogue.

Further, the molar ratio of the active ingredient in the polymer matrix layer to the amino group in the compound containing at least one amino group is about 12:1 to about 1:1, including about 10:1 to about 1.5:1, such as about 10:1, about 9:1, about 8:1, about 7:1, about 6:1, about 5:1, about 4:1, about 3:1, about 2:1, and about 1.5:1. Studies have found that if the molar ratio of the active ingredient to the amino group in the amino compound is higher than 15:1, the transdermal penetration efficiency of ibuprofen or its structural analogue in the transdermal drug delivery system will be reduced, and the delivery capacity will not meet the requirements of therapeutic effects, also resulting in the decrease of the drug loading capacity of ibuprofen or its structural analogue in the polymer matrix; if the ratio is less than 1:1, the formed active ingredient-amino compound salt has a decreased melting point or is in a liquid state at room temperature, which leads to poor colloidal properties of the polymer matrix, especially the decrease of the cohesion of the colloid. As a result, after the patch is applied, there will be serious problems such as cobwebbing at the application site and residual paste on the skin.

Further, the content by weight of the compound containing at least one amino group in the polymer matrix layer of the patch (referring to the ratio by weight of the compound containing at least one amino group to the dry weight of the polymer matrix layer) is about 1% to about 15%, including about 2% to about 12%, such as about 2%, about 3%, about 4%, about 5%, about 6%, about 7%, about 8%, about 9%, about 10%, about 11%, and about 12%.

The compound containing at least one amino group is preferably an aliphatic amine, which may be a chain amine or a cyclic amine. The compound containing at least one amino group may be a primary amine, a secondary amine or a tertiary amine. The compound containing at least one amino group may contain 1 to 4 amino groups, such as one amino group, two amino groups, three amino groups, and four amino groups. The compound containing at least one amino group includes but is not limited to the following compounds: one or more of ethanolamine (Am_1), diethanolamine (Am_2), triethanolamine (Am_3), diethylamine (Am_4), triethylamine (Am_5), propylene diamine (Am_6), N-ethylmorpholine (Am_7), N-ethylpiperidine (Am_8), N-ethylpiperazine (Am_9), N-hydroxyethylpiperidine (Am_10), N-hydroxyethylpyrrole (Am_11), dimethylpropanediamine (Am_12), tetramethylpropanediamine (Am_13), N-dodecylpyrrole (Am_14), trihexylamine (Am_15), N-dodecyl homopiperidine (Am_16), pyridin-2-yl-methanol (Am_17), ethylenediamine (Am_18), tetramethylethylenediamine (Am_19), spermidine (Am_20), spermine (Am_21), cyclen (Am_22), 3-(piperazin-1-yl)propan-1,2-diol (Am_23), N-hydroxyethylpiperazine (Am_24), N-methylmorpholine (Am_25), triethylenediamine (Am_26), tris(2-aminoethyl)amine (Am_27), 2-piperazinone (Am_28), 3-aminopiperidine (Am_29), 1,3-cyclohexanedimethylamine (Am_30), propylene glycol bis(3-aminopropyl) ether (Am_31), ethylene glycol bis(3-aminoethyl) ether (Am_32) and the like.

If there is any inconsistency between the chemical name and the chemical structure of the compound containing at least one amino group, the following chemical molecular structure shall prevail.

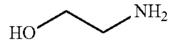

Am_1

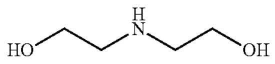

Am_2

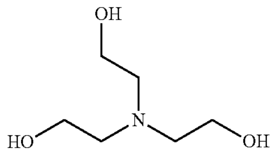

Am_3

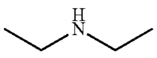

Am_4

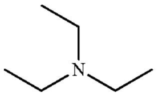

Am_5

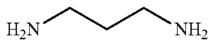

Am_6

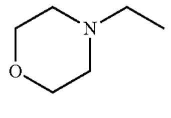

Am_7

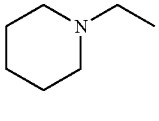

Am_8

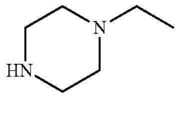

Am_9

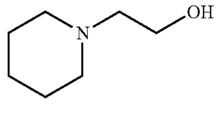

Am_10

-continued

Am_11

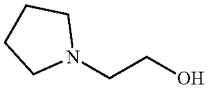

Am_12

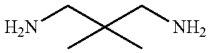

Am_13

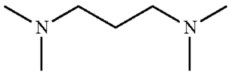

Am_14

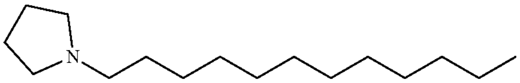

Am_15

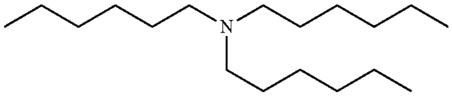

Am_16

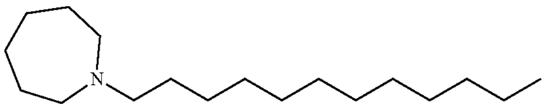

Am_17

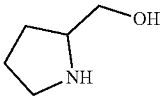

Am_18

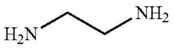

Am_19

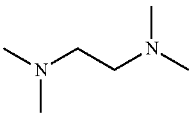

Am_20

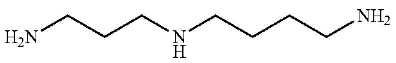

Am_21

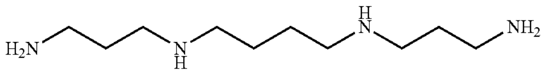

Am_22

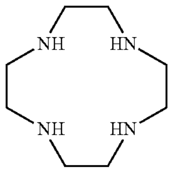

Am_23

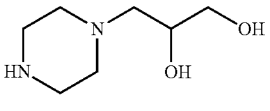

Am_24

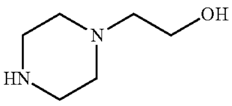

-continued

Am_25

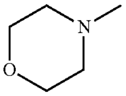

Am_26

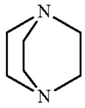

Am_27

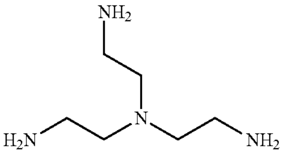

Am_28

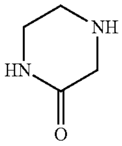

Am_29

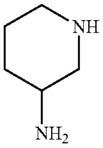

Am_30

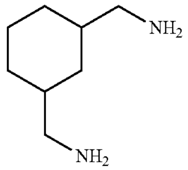

Am_31

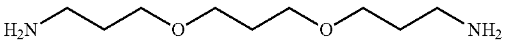

Am_32

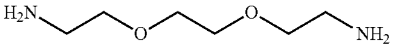

The amount of the active ingredient (i.e., ibuprofen or its structural analogue) added to the polymer matrix in the patch of the present invention varies according to the required therapeutic effect and the application time range of the patch. The active ingredient enters the skin from the patch through passive diffusion, which is the step that determines the speed of transdermal absorption. Therefore, the minimum dose required by this means depends on the lowest onset concentration achieved for a therapeutic effect during the application of the patch. The patch of the present invention is generally used for 12 to 24 hours, so in some examples, the patch of the present invention can continuously and controllably deliver a therapeutically effective amount of drug within 12 to 24 hours. In some examples, the content by weight of the active ingredient in the polymer matrix layer of the patch (referring to the ratio of the weight of the active ingredient to the dry weight of the polymer matrix layer) is about 15% to about 45%, including about 20% to about 40%, such as about 20% to about 35%, more preferably in the range of about 25% to about 35%. In some special examples, the content by weight of the active ingredient in the polymer matrix layer is 25%. In some special examples, the content by weight of the active ingredient in the polymer matrix layer is 30%, and in some special examples, the content by weight of the active ingredient in the polymer matrix layer is 35%.

The Pressure-Sensitive Adhesive in the Polymer Matrix Layer of the Patch:

As mentioned above, the polymer matrix layer of the patch of the present invention comprises at least one pressure-sensitive adhesive that is pharmaceutically suitable for a transdermal drug delivery system, which can be specifically selected from acrylic-based polymer compounds or polysilicone polymer compounds, or combination thereof, or composite thereof.

In some examples, the polymer matrix comprises acrylic polymer compounds. According to the difference in monomers selected during polymerization, the acrylic polymer can be any homopolymer, copolymer, trimer, or polymer of different acrylic acids. According to the difference in functional groups contained, it can be a non-functionalized acrylic pressure-sensitive adhesive and a functionalized acrylic pressure-sensitive adhesive.

The non-functionalized acrylic pressure-sensitive adhesive comprises any acrylic polymer that does not contain or essentially does not contain functional groups (such as carboxyl, hydroxyl, amino, epoxy and the like), and the acrylic polymer includes polyacrylate and polyacrylamide or corresponding methacrylic acid derivatives. The functionalized acrylic pressure-sensitive adhesive comprises chemically active groups, such as carboxyl, hydroxyl, amino, epoxy and the like.

In some examples, based on the difference in the amount of the active ingredient (i.e. ibuprofen or its structural analogue) added and the difference in the amount to be delivered to achieve the therapeutic effect, the type and amount of acrylic polymers are also different. In some examples, the acrylic pressure-sensitive adhesive accounts for about 40% to about 80% of the dry weight of the polymer matrix, preferably about 45% to about 75%, such as about 45% to about 70%, including about 45%, about 50%, about 55%, about 60%, about 65%, and about 70%. In some special examples, a functionalized acrylic pressure-sensitive adhesive can be selected. In some special examples, a non-functionalized acrylic pressure-sensitive adhesive or a combination of functionalized acrylic pressure-sensitive adhesive and non-functionalized acrylic pressure-sensitive adhesive can be selected. The specific proportion is determined according to the performance requirements of the patch, and can be selected according to the conventional experiments. The acrylic pressure-sensitive adhesive without functional groups is preferred, or when a combination of the functionalized acrylic pressure-sensitive adhesive and the non-functionalized acrylic pressure-sensitive adhesive is used, it is preferable that the non-functionalized acrylic pressure-sensitive adhesive accounts for a larger proportion.

Commercially available polyacrylic pressure-sensitive adhesives include Henkel's Duro-Tak products, such as Duro-Tak 87-900A, Duro-Tak 87-9900, Duro-Tak 87-9301 (non-crosslinked, acrylic pressure-sensitive adhesive without vinyl acetate and functional groups), Duro-Tak 87-4098 (non-crosslinked vinyl acetate acrylic pressure-sensitive adhesive without functional groups), Duro-Tak 87-2287 (non-crosslinked vinyl acetate acrylic pressure-sensitive adhesive with hydroxyl functional groups), Duro-Tak 87-2852 (cross-linked acrylic pressure-sensitive adhesive with carboxyl functional groups), Duro-Tak 87-2196 (cross-linked acrylic pressure-sensitive adhesive with carboxyl functional groups), Duro-Tak 87-2296 (cross-linked acrylic pressure-sensitive adhesive with carboxyl functional group), Duro-Tak 87-2194 (cross-linked acrylic pressure-sensitive adhesive with carboxyl functional groups), Duro-Tak 87-2516 (cross-linked acrylic pressure-sensitive adhesive with carboxyl functional groups), Duro-Tak 87-2070 (cross-linked acrylic pressure-sensitive adhesive with carboxyl functional group), Duro-Tak 87-2353 (non-cross-linked acrylic pressure-sensitive adhesive with carboxyl functional group), Duro-Tak 87-2154 (cross-linked acrylic pressure-sensitive adhesive with carboxyl functional groups), and Duro-Tak 87-2510 (non-cross-linked acrylic pressure-sensitive adhesive with hydroxyl functional groups). For more product information, please refer to the professional books: Handbook of Pressure Sensitive Adhesive Technology, second edition, author: Donatas Satas, Publisher: New York: Van Nostrand Reinhold, 1989; and Technology of Pressure-Sensitive Adhesives and Process, Editor-in-Chief: Istvan Benedek, Mikhail M Feldstein, Publisher: CRC press, 2009.

In some examples, the polymer matrix may comprise a polysilicone polymer pressure-sensitive adhesive. The polysilone pressure-sensitive adhesive is not used alone in the first combined layer due to its relatively high drug diffusion rate but less solubility of the active ingredient ibuprofen or its structural analogue, and incompatibility with the acrylic pressure-sensitive adhesive. In some special examples, it is used in combination with at least one polyacrylic pressure-sensitive adhesive. In some special examples, the dry ratio by weight of the polysilicone pressure-sensitive adhesive in the polymer matrix is about 0% to about 10%, preferably about 1% to about 5%, including about 1.5%, about 2%, about 2.5%, about 3%, about 3.5%, about 4%, about 4.5%, and about 5%.

In some special examples, the polymer matrix comprises a composite of the polysilicone polymer pressure-sensitive adhesive and the polyacrylic polymer pressure-sensitive adhesive. The silicone polymer has a relatively high drug diffusion rate, does not irritate the skin, and has good chemical stability, and the acrylic pressure-sensitive adhesive has a relatively high dissolving ability. However, due to the large difference in the properties of these two types of adhesives, only a suspension form can be formed by ordinary physical mixing, resulting in the limitation of the amount of polysilicone adhesive. In the present invention, the polysilicone pressure-sensitive adhesive and the polyacrylic pressure-sensitive adhesive are cross-linked by chemical means to form a new polysilicone-polyacrylic composite polymer pressure-sensitive adhesive, and the composite pressure-sensitive adhesive balances the properties of the acrylic pressure-sensitive adhesive and the polysilicone pressure-sensitive adhesive, and can form a uniformly mixed homogeneous phase. In some examples, the ratio by weight of the polysilicone-polyacrylic composite polymer to the polymer matrix is about 40% to 80%, preferably about 45% to 75%, including about 45%, about 50%, 55%, and 60%.

Commercially available polysilicone pressure-sensitive adhesives include products of Dow Corning, such as Dow Corning® 7-6102 SilAc Hybrid PSA; Dow Corning® 7-6302 SilAc Hybrid PSA; and products of Bio-PSA, Such as Bio-PSA 7-4502, Bio-PSA 7-4602, Bio-PSA 7-4302 and Bio-PSA 7-4102.

Further, the polymer matrix layer of the transdermal patch containing ibuprofen or its structural analogue may also contain pharmaceutically usable auxiliary materials.

Fillers in the Polymer Matrix Layer of the Patch:

As mentioned above, both the ibuprofen itself and the ibuprofen-amino compound salt have a tackifying effect on the polymer matrix, resulting in a decrease in the cohesion of the polymer matrix, and serious cobwebbing and residues of the patch at the application on skin, and the colloidal properties of the patch cannot meet the requirements of wearing, which brings another serious challenge when developing the present invention. Through a large number of experiments, the present invention has surprisingly found that the addition of pharmaceutically acceptable fillers can improve or solve the problem of colloidal performance without reducing the overall transdermal permeation rate of the active ingredient ibuprofen.

The present disclosure discovers that an appropriate amount of filler added increases the overall cohesion of the polymer matrix, thereby reducing the problems such as cobwebbing and residues of the polymer matrix on the skin surface after application. However, when the cohesion is increased, the adhesion and peel adhesion will be decreased. Without relation to any theory, because the cohesion, adhesion, peel adhesion and shear resistance of the pressure-sensitive adhesive are mutually dependent, change of one of the properties will also cause the change of other properties. It is difficult to achieve the sole improvement of the cohesion or adhesion without affecting other properties, or without destroying the mechanical properties of the overall adhesive system of the pressure-sensitive adhesive. The change of cohesion varies with the change of the corresponding adhesion. Through this change, the colloidal properties of the polymer matrix containing ibuprofen and amino compounds can be adjusted by the addition of fillers, so that the pressure-sensitive adhesive has suitable cohesion to achieve no cobwebbing and no residues of adhesives after application, as well as acceptable adhesion, peel adhesion and shear resistance.

In some examples, the polymer matrix layer contains fillers. The average particle size of the filler is about 300 mesh to about 5,000 mesh, including about 500 mesh to about 3,000 mesh. The surface area of the filler is about 1.5 $m^2/g$ to about 15 $m^2/g$, including about 3 $m^2/g$ to about 10 $m^2/g$, and about 4 $m^2/g$ to about 7 $m^2/g$. The fillers include, but are not limited to, any one or more of talc, bentonite, kaolin, colloidal silica, montmorillonite and the like.

Further research has found that the filler in the polymer matrix layer cannot be a metal oxide (such as titanium dioxide, zinc oxide, and magnesium oxide), or an inorganic salt (such as sodium carbonate, and magnesium carbonate). Because these fillers will cause a serious decrease in the penetration rate of ibuprofen or its structural analogue.

In some examples, the amount of filler contained in the polymer matrix accounts for about 0.5% to about 10% by weight of the total dry polymer matrix, preferably in the range of about 1% to about 10%, and more preferably about 2% to about 8%, such as about 2%, about 3%, about 4%, about 5%, about 6%, about 7%, and about 8%. The specific amount of the filler added needs to be determined comprehensively according to the amount of the active ingredient and amino-containing compounds in the polymer matrix, as well as the type, property and proportion of the pressure-sensitive adhesive used, and thus, the mechanical properties of the adhesive can be precisely controlled without affecting the diffusion rate of the active ingredient to meet the wearing requirements.

Antioxidants in the Polymer Matrix Layer of the Patch:

In some examples, the polymer matrix layer further comprises antioxidants. The antioxidants include 2,6-di-tert-butyl-4-methylphenol (BHT), butylhydroxyanisole (BHA), tert-butyl hydroquinone (TBHQ), vitamin C, vitamin E, sodium ascorbate, sodium pyrosulfite, polyethylene glycol vitamin E succinate (TPGS), L-ascorbyl palmitate and a mixture of these antioxidants. The content of antioxidants in the polymer matrix is about 0.1% to about 1%, preferably about 0.1% to about 0.5% of the total weight of the dry matrix.

Transdermal Enhancer:

The present invention has unexpectedly found that the commonly used transdermal enhancers in the transdermal absorption system could not achieve the expected effect of increasing the diffusion rate in this system. On the contrary, after addition of different transdermal enhancers, the penetration rate in some special examples is basically unchanged, or in some special examples, the penetration rate of ibuprofen or its structural analogue is suppressed. The transdermal enhancers include but are not limited to different types of transdermal enhancers with different mechanisms, such as propylene glycol, PEG600, olive oil, squalene, silicone oil, mineral oil, oleic acid, isopropyl myristate, cetyl palmitate, propylene glycol monocaprylate, caprylic/capric triglyceride, ethyl oleate, oleoyl polyoxyl-6 glycerides, urea, azone, N-methylpyrrolidone, dimethyl sulfoxide (DMSO), glycerin and the like. The transdermal enhancers are used alone or in combination in some examples. The content of the transdermal enhancer in the polymer matrix is about 0.5% to about 5%, preferably about 1% to about 5%, such as about 1%, about 2%, about 2.5%, and about 3% of the total weight of the dry polymer matrix. Since transdermal enhancers are basically liquid or oily, the addition of transdermal enhancers to the polymer matrix of the present invention will further increase the fluidity of the matrix, which may lead to difficulties in flowing for some reason without relation to any theory. Therefore, the transdermal enhancer does not help the penetration efficiency of the transdermal drug delivery system of ibuprofen or its structural analogue of the present invention, and the present invention does not need to add any transdermal enhancer.

The patch of the present invention contains an active ingredient (i.e. ibuprofen or its structural analogue) accounting for about 15% to 45% of the dry weight of the polymer matrix, and amino compounds partially or completely used for salt formation, and successfully solves the problems of diffusion rate, high loading drug and stability of ibuprofen or its structural analogue.

Specifically, in the polymer matrix layer of the patch of the present invention, the content by weight of the active ingredient (i.e. ibuprofen or its structural analogue) is about 15% to about 45%, and the content by weight of the compound containing at least one amino group is about 1% to about 15%. The molar ratio of the active ingredient to the amino group in the compound containing at least one amino group is about 12:1 to about 1:1. The active ingredient and the compound containing at least one amino group totally form salt or partly form salt. The active ingredient is uniformly dispersed or dissolved in the polymer matrix, and can be stored stably for a long time. Ibuprofen or its structural analogue will not recrystallize, and thus it can be delivered continuously and stably in a therapeutically effective amount for at least 12 to 24 hours.

In some examples, the patch of the present invention can continuously increase the blood drug concentration within 8 hours, and then the blood drug concentration will steadily decrease in the following 4 hours, achieving a stable clinical effect for 12 hours.

The Second Combined Layer:

Due to the combined tackifying effect of the active ingredient (i.e., ibuprofen or its structural analogue) and the active ingredient-amino compound salt on the polymer matrix, the overall cohesion of the polymer matrix is reduced, resulting in problems of serious cobwebbing and residues formed on the skin after application of the patch, severely affecting the patient's compliance with wearing of the patch, and there is a risk of slipping or falling off when the patch is worn for a long time. The present invention solves the problem of residues on the skin caused by the tackifying effect of the active ingredient and the active ingredient-amino compound salt by adding a solid filler to regulate the cohesion of the polymer matrix. However, due to the addition of fillers, the optimization of cohesion is accompanied by loss of adhesion. On the other hand, due to the ubiquitous cold flow phenomenon of the patch, one of the consequences is that after the patch is applied, the adhesive left around the patch will mix with the dust in the environment to form a black circle, which will affect the safety of use and the patient compliance. Therefore, another problem to be solved by the present invention is to satisfy good wearing performance, and the patch can be worn safely and comfortably during 12 to 24 hours of use.

In order to solve the above problems, the present invention also provides a multi-layer transdermal drug delivery system containing ibuprofen or its structural analogue, and the system comprises the above-mentioned transdermal patch containing ibuprofen or its structural analogue (may be called a first combined layer), and also comprises a second combined layer.

The second combined layer comprises a backing layer, a protective layer, and a polymer matrix layer located between the backing layer and the protective layer. The polymer matrix layer comprises a pressure-sensitive adhesive.

The present invention has unexpectedly found that the above problems are greatly reduced or avoided with such a design of a multi-layer structure by adding a second combined layer, and a transdermal ibuprofen drug delivery system meeting the wearing requirements is provided. The multi-layer transdermal drug delivery system of the present invention has good performance, meets the wearing requirements, does not slip off during the application process, has no residues, and no damage to the skin when stripped. The patch has good safety during storage and use, and has good patient wearing compliance.

The function of the second combined layer is to provide a transdermal drug delivery system of ibuprofen or its structural analogue that meets the wearing requirements. In addition to the backing layer and the protective layer of the second combined layer, the polymer matrix layer located between the two layers comprises a pressure-sensitive adhesive, and may also comprise a pharmaceutically acceptable auxiliary material, and/or may further comprise the active ingredient (i.e., ibuprofen or its structural analogue) or other active ingredients. Whether the polymer matrix layer of the second combined layer contains active ingredients such as ibuprofen has no substantial effect on solving the cold flow problem of the polymer matrix layer of the first combined layer. It can be determined according to actual needs whether to add active ingredients such as ibuprofen to the polymer matrix layer of the second combined layer. Further research has found that if the polymer matrix layer of the second combined layer contains ibuprofen or its structural analogue, the content of ibuprofen or its structural analogue cannot be too high, and if the content exceeds 15%, the aforementioned cold flow problem cannot be solved. Therefore, the content by weight of ibuprofen or its structural analogue in the polymer matrix layer of the second combined layer may be ≤15%, for example, ≤10%, ≤8%, or ≤5%.

In some examples, the polymer matrix layer of the second combined layer comprises at least one of pharmaceutically acceptable polyacrylic pressure-sensitive adhesive, polysilicone pressure-sensitive adhesive, rubber, or a mixture of two or more thereof. In some special examples, the pressure-sensitive adhesive may be a styrene-isobutylene-styrene (SIS) polymer block. In some examples, the polymer matrix may also comprise other pharmaceutically acceptable auxiliary materials, such as antioxidants, plasticizers, and fillers.

As mentioned above, the present invention has found that the use of the second combined layer can enable the transdermal drug delivery system of ibuprofen or its structural analogue to have satisfactory wearing performance, so as to achieve a satisfactory delivery dose within 12 to 24 hours of use.

Before use, the separate transdermal patch containing ibuprofen or its structural analogue and the second combined layer are combined together to form the multi-layer ibuprofen transdermal drug delivery system of the present invention.

For example, before the use of the multi-layer transdermal drug delivery system containing ibuprofen or its structural analogue, the protective layer of the second combined layer can be removed such that the second combined layer can attach to the backing layer of the transdermal patch containing ibuprofen or its structural analogue, and then the protective layer of the transdermal patch is removed to attach the patch to the application site (for example, the skin of a patient). Alternatively, the protective layer of the transdermal patch is first removed to attach the patch to the application site (for example, the skin of a patient), and then the protective layer of the second combined layer is removed to attach the second combined layer to the backing layer of the transdermal patch. The above two methods have no difference in the use effect.

The transdermal drug delivery system of ibuprofen or its structural analogue of the present invention can continuously and controllably deliver a therapeutically effective amount of drug within 12 to 24 hours of use without the use of a transdermal enhancer, which meets the needs of clinical use.

In some special examples, the patch of the present invention can continuously increase the blood drug concentration within 16 hours, and then the blood drug concentration will steadily decrease in the following 8 hours, achieving a stable clinical effect for 24 hours. Therefore, without using a transdermal enhancer, the present invention can deliver a therapeutically effective dose of ibuprofen or its structural analogue within 12 to 24 hours according to the requirements of the therapeutic effect.

The present invention can be applied to reduce fever, such as high fever in children of 6 months to 36 months old. The present invention can also be used for relieving pain, such as relieving local pain.

In some examples, the thickness of the dry polymer matrix layers in the transdermal patch containing ibuprofen or its structural analogue and/or the second combined layer is about 10 μm to about 120 μm, preferably about 15 μm to about 80 μm.

Preferably, the peripheral width of the second combined layer is slightly wider than the peripheral width of the transdermal patch containing ibuprofen or its structural analogue, and more preferably about 0.5 cm to about 1.0 cm wider than the peripheral width of the transdermal patch containing ibuprofen or its structural analogue.

Further, the polymer matrix layer in the transdermal patch and/or the second combined layer is a single-layer structure.

In some examples, both the transdermal patch and the second combined layer of the present invention include a separate backing layer and a separate protective layer. One surface of the backing layer is directly connected with the polymer matrix layer, and when in use, the backing layer protects the matrix layer from contact with the surrounding environment and prevents the loss of drugs. The material of the backing layer generally comprises polyester, composite film of polyester and vinyl acetate, composite film of polyethylene and vinyl acetate, polyurethane, metal foil such as metal aluminum lined polyester, non-woven fabric and the like. The thickness is generally about 20 to 250 μm, preferably 20 to 100 μm, such as ScotchPak™ 1109 and ScotchPak™ 9733 from 3M Company, or Cotran™ 9720 and Cotran™ 9722 from 3M Company. The release film is connected to the other side of the polymer matrix layer. The material of the release film generally comprises polyester, polypropylene and the like, and the release film generally has a fluoride coating on the surface. The thickness is generally about 50 to 100 μm, preferably 60 to 80 μm, such as ScotchPak™ 9744 and ScotchPak™ 9755 from 3M Company.

The transdermal patch and the second combined layer of the present invention can be prepared separately. For the transdermal patch containing ibuprofen or its structural analogue, first, the polymer matrix portion of the transdermal drug delivery system is prepared, the following substances in amounts calculated based on the prescription are added into a suitable organic solvent: the active ingredients, pressure sensitive adhesives, amino compounds, and auxiliary materials including fillers and oxidants (if auxiliary materials are further included), after being stirred well, the resultant is coated onto a protective layer (release film) at room temperature, the coated polymer matrix is then dried at a certain temperature to remove the organic solvent, and finally the backing layer is combined. Punching or cutting is performed according to the requirements to obtain specifications as required.

The organic solvent is a solvent capable of dissolving ibuprofen or its structural analogue, pressure-sensitive adhesives and amino compounds, including ethyl acetate, methanol, ethanol, isopropanol, toluene, acetonitrile, acetone and the like.

It should be noted that the order involved in the above preparation of the transdermal patch containing ibuprofen or its structural analogue, the addition amount of each component, and the parameters such as stirring time and stirring speed may vary according to different final use purposes as required. The parameters can be adjusted as needed.

The preparation method involved in the present invention can refer to methods disclosed in literatures. For example, according to the conventional method reported in the literature, the polymer matrix is coated on the release film, and then combined with the backing layer to form a transdermal drug delivery system, and finally different specifications are made according to the needs of use. The general coating method is solution coating. In some examples, a polymer matrix is prepared after mixing all the components, and then the prepared polymer matrix is coated on a release film, placed at about 35° C. to 50° C. to remove the solvent, and then combined with the backing layer. The active ingredient and a solid filler can be added at any stage as required. In some examples, first, a polymer pressure-sensitive adhesive and an amino compound are dissolved in an organic solvent and stirred evenly, then the active ingredient is added and stirred to be completely dissolved, and finally a solid filler is added. In some examples, first, ibuprofen or its structural analogue is dissolved in an organic solvent, and then a polymer pressure-sensitive adhesive and an amino compound are added successively, the above mixture is stirred evenly, then a solid filler is added, and then the resultant is stirred to be uniformly dispersed. The amount of each component added, the order of addition, and the stirring time can be determined by a person skilled in the art through experiments. An exemplary preparation method is as follows:

Step 1): Firstly, a calculated amount of a polymer pressure-sensitive adhesive is added to a suitable organic solvent. The stirring time is determined by whether the mixture is uniform, generally about 15 to 30 minutes. Then, while keeping stirring, an amino compound and an antioxidant are added, and the resultant is stirred to be completely dissolved. Then, the active ingredient is added in batches, gradually dissolved under stirring, and then the next batch of the active ingredient is added until all of the active ingredient is added and dissolved. Finally, a solid filler is added and stirred to be completely and uniformly dispersed.

Step 2): The mixed solution prepared in step 1) is coated on a release film, with a coating thickness determined according to the needs of the final clinical use.

Step 3): The organic solvent is removed by drying at 35° C. to 50° C. for 5 to 15 minutes in an oven with exhaust function.

Step 4): The dried product is combined with a selected suitable backing film.

Step 5): Punching or cutting is performed to obtain suitable specifications according to the needs of use.

Based on the general preparation method of the patch, other methods reported in the literature can also be used for the preparation of the patch of the present invention.

The second combined layer of the present invention can be prepared with reference to the preparation method of the transdermal patch described above.

In some examples, the content of the active ingredient (i.e., ibuprofen or its structural analogue) contained in the polymer matrix of the patch of the present invention ranges from about 0.8 mg/cm$^2$ to about 4.0 mg/cm$^2$, including from about 1.2 mg/cm$^2$ to about 3.2 mg/cm$^2$, from about 1.5 mg/cm$^2$ to about 2.9 mg/cm$^2$, such as about 1.6 mg/cm$^2$, about 1.9 mg/cm$^2$, about 2.2 mg/cm$^2$, about 2.3 mg/cm$^2$, about 2.4 mg/cm$^2$, about 2.6 mg/cm$^2$, and about 2.9 mg/cm$^2$. According to the blood drug concentration that needs to be achieved within the application time range, the administration area of the patch of the present invention ranges from about 10 cm$^2$ to about 150 cm$^2$, including from about 20 cm$^2$ to about 120 cm$^2$, such as 20 cm$^2$, 30 cm$^2$, 40 cm$^2$, 50 cm$^2$, 60 cm$^2$, 70 cm$^2$, and 80 cm$^2$. In some special examples, the patch of the present invention can continuously increase the blood drug concentration within 8 hours, and then the blood drug concentration will steadily decrease in the following 4 hours, achieving a stable clinical effect for 12 hours. In some special examples, the patch of the present invention can continuously increase the blood drug concentration within 16 hours, and then the blood drug concentration will steadily decrease in the following 8 hours, achieving a stable clinical effect of 24 hours. Therefore, the present invention can deliver a therapeutically effective dose of ibuprofen or its structural analogue within 12 to 24 hours according to the requirements of the therapeutic effect.

In some examples, the present invention is applied to reduce fever, such as high fever in children of 6 months to 36 months old. In some examples, the present invention is used for relieving pain, such as relieving local pain.

SPECIFIC MODES FOR CARRYING OUT THE EMBODIMENTS

Figure 1:
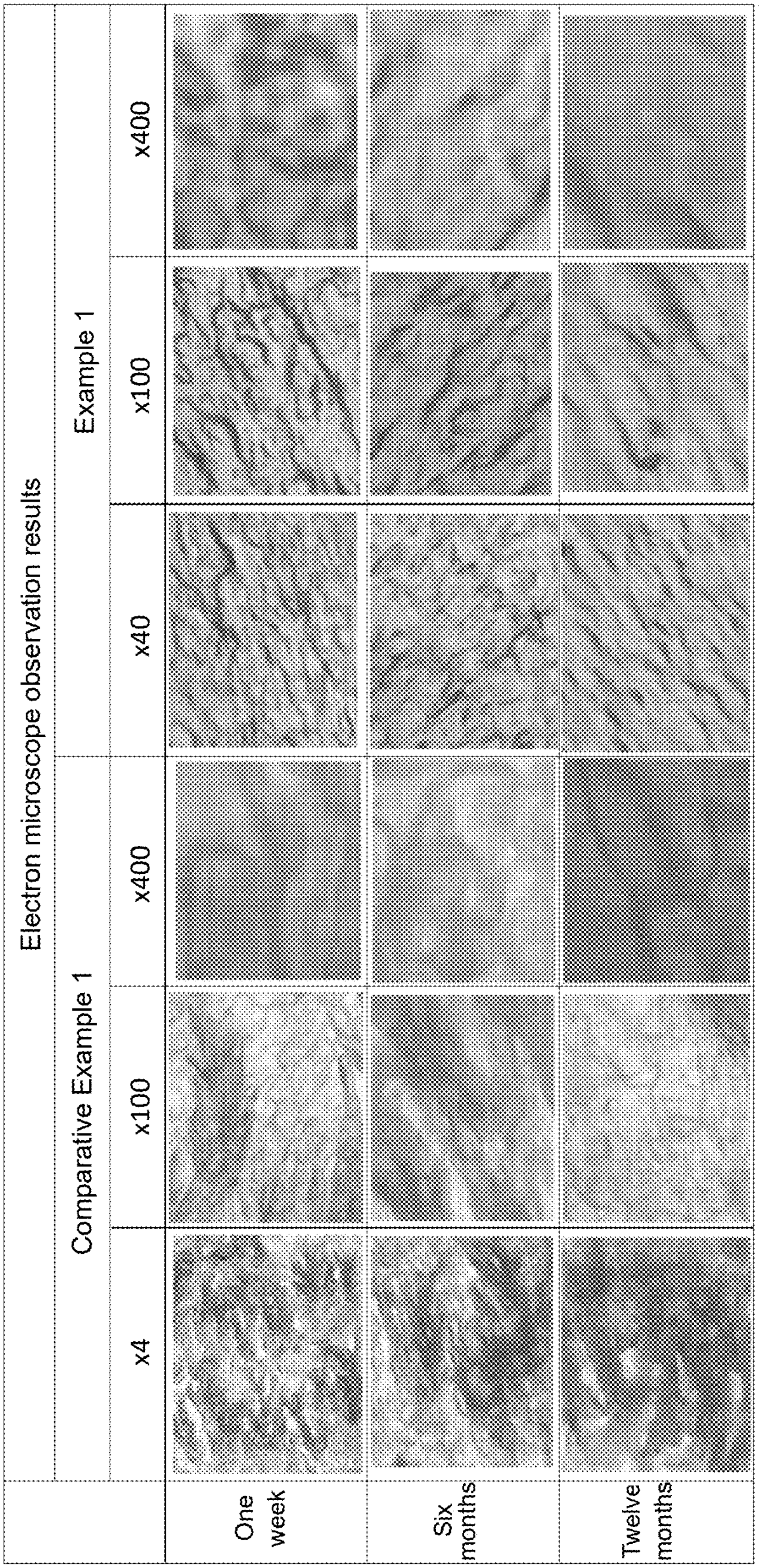
FIG. 1 shows the results of the stability experiment of Experimental Example 1.

The following Examples are intended to illustrate the present invention, but are not intended to limit the scope of the present invention. If the specific technology or conditions are not indicated in the Examples, it shall be carried out according to the technology or conditions described in the literature in the art or according to the product specification. If the manufacturer is not indicated, the reagents or instruments used are conventional products that can be purchased through regular channels.

In the following examples, Dow Corning® 7-6102 is a composite of acrylic pressure-sensitive adhesive and polysilicone pressure-sensitive adhesive. Duro-tack-4098 is a pressure-sensitive adhesive of a copolymer of acrylic acid and vinyl acetate, containing no functional groups and no crosslinking agents. Duro-tack-2074 is an acrylic pressure-sensitive adhesive containing carboxyl and hydroxyl functional groups and a crosslinking agent. Duro-tack-6908 is a polyisobutylene pressure-sensitive adhesive containing no functional groups and no crosslinking agents. Bio-PSA-7-4302 is a polysilicone pressure-sensitive adhesive. Tert-butyl-4-hydroxyanisole (BHA) is an antioxidant.

Example 1

An ibuprofen-containing transdermal patch comprises a polymer matrix layer. The polymer matrix layer comprises an active ingredient ibuprofen, a compound containing at least one amino group, and a pressure-sensitive adhesive. In the polymer matrix layer, all or part of ibuprofen forms a salt with the compound containing at least one amino group, and all or part of ibuprofen-amino compound salt and all or part of free ibuprofen formed are kept uniformly dissolved in the polymer matrix, and can be stored stably without recrystallization before use.

Further, the transdermal patch of the present Example further comprises a backing layer and a protective layer. The polymer matrix layer was located between the backing layer and the protective layer.

In the present Example, in the polymer matrix layer, the content by weight of ibuprofen was 35%, the content by weight of the pressure-sensitive adhesive was 54% (wherein the content by weight of Duro-tack-4098 was 50%, and the content by weight of Bio-PSA-7-4302 was 4%), and the content by weight of the compound containing one amino group (specifically Am 25) was 5%. In addition, the polymer matrix layer can also contain pharmaceutically acceptable auxiliary materials (such as talc, colloidal $SiO_2$, montmorillonite, and vitamin E).

The present Example also provides a preparation method of the transdermal patch, comprising: firstly, a calculated amount of a polymer pressure-sensitive adhesive was weighed, and added to an appropriate amount of ethyl acetate, and then an amino compound was added, and further auxiliary materials (if present) such as an antioxidant (for example, vitamin E) were added while keeping stirring. The stirring time was determined by whether the mixture was uniform, generally about 15 to 30 minutes. After stirring to be completely dissolved, the active ingredient ibuprofen was added in batches. After gradually dissolving under stirring, the next batch of ibuprofen was added until all of the active ingredient ibuprofen was added and dissolved. Finally, a solid filler was added and stirred to be completely and uniformly dispersed. The prepared polymer matrix was coated on a release film, with a coating thickness determined according to the needs of the final clinical use. The coated polymer matrix was dried in an oven with exhaust function at 35° C. to 50° C. for 5 to 15 minutes to remove the organic solvent. The dried product is then combined with a suitable backing film. Finally, cutting was performed to obtain suitable specifications according to the needs of use, and the final product was packaged.

The formulations of the polymer matrix layer of a typical transdermal patch containing ibuprofen (Examples 1-10) were shown in Table 1 (for the preparation method, refer to Example 1).

TABLE 1

(Table 1 shows the percentage by weight.)

| Example | Ibuprofen | Duro-tack-4098 | Dow Corning ®7-6102 | Bio-PSA-7-4302 | Am_9 | Am_13 | Am_25 | Talc | Colloidal $SiO_2$ | Montmorillonite | Vitamin E |
|---|---|---|---|---|---|---|---|---|---|---|---|
| 1 | 35 | 50 | | 4 | | | 5 | 5 | | | 1 |
| 2 | 20 | 71 | | 5 | 2 | | | 1 | | | 1 |
| 3 | 25 | 69 | | | | 3 | | | 2 | | 1 |
| 4 | 30 | 63 | | | | | 3 | 3 | | | 1 |
| 5 | 35 | 54 | | | 5 | | | | | 5 | 1 |
| 6 | 40 | 45 | | | | 7 | | | 7 | | 1 |
| 7 | 30 | | 60 | | | 5 | | | 4 | | 1 |

TABLE 1-continued (Table 1 shows the percentage by weight.)

| Example | Ibuprofen | Duro-tack-4098 | Dow Corning ®7-6102 | Bio-PSA-7-4302 | Am_9 | Am_13 | Am_25 | Talc | Colloidal $SiO_2$ | Montmoril-lonite | Vitamin E |
|---|---|---|---|---|---|---|---|---|---|---|---|
| 8 | 30 | | 60 | | | 5 | | | | 4 | 1 |
| 9 | 30 | 57 | | 4 | | | 5 | | | 3 | 1 |
| 10 | 35 | 58 | | | 2 | | | | 4 | | 1 |
| Comparative Example 1 | 20 | 78 | | | | | | 1 | | | 1 |

Comparative Example 1

A transdermal patch containing ibuprofen, the formulation of the polymer matrix layer thereof was shown in Table 1, and for the preparation method, refer to Example 1.

Examples 11-21

The formulations of the polymer matrix layer of the transdermal patch of ibuprofen containing different types of transdermal enhancers (i.e., Examples 11-21) and the change in the penetration efficiency were shown in Table 2 (for the preparation method, refer to Example 1).

TABLE 2

(Table 2 shows the percentage by weight.)

| Example | Ibuprofen | Duro-tack-2074 | Am_10 | Talc | Vitamin E | Silicone oil Q7-9120 | Propylene glycol | Diethylene glycol monoethyl ether | Isopropyl oleate |
|---|---|---|---|---|---|---|---|---|---|
| 11 | 35 | 53 | 5 | 5 | 1 | 1 | | | |
| 12 | 35 | 53 | 5 | 5 | 1 | | 1 | | |
| 13 | 35 | 53 | 5 | 5 | 1 | | | 1 | |
| 14 | 35 | 53 | 5 | 5 | 1 | | | | 1 |
| 15 | 35 | 53 | 5 | 5 | 1 | | | | |
| 16 | 35 | 53 | 5 | 5 | 1 | | | | |
| 17 | 35 | 53 | 5 | 5 | 1 | | | | |
| 18 | 35 | 53 | 5 | 5 | 1 | | | | |
| 19 | 35 | 53 | 5 | 5 | 1 | | | | |
| 20 | 35 | 53 | 5 | 5 | 1 | | | | |
| 21 | 35 | 53 | 5 | 5 | 1 | | | | |

| Example | Menthol | Azone | Oleic acid | Tween-80 | Urea | Azo methyl pyrrolidone | Squalane | Change in penetration efficiency |
|---|---|---|---|---|---|---|---|---|
| 11 | | | | | | | | C |
| 12 | | | | | | | | B |
| 13 | | | | | | | | B |
| 14 | | | | | | | | A |
| 15 | 1 | | | | | | | B |
| 16 | | 1 | | | | | | B |
| 17 | | | 1 | | | | | B |
| 18 | | | | 1 | | | | C |
| 19 | | | | | 1 | | | C |
| 20 | | | | | | 1 | | C |
| 21 | | | | | | | 1 | A |

A = almost no change in penetration;
b = slight decrease in penetration;
C = significant decrease in penetration It can be seen from the results in Table 2 that the addition of different types of transdermal enhancers basically does not improve the penetration efficiency, but hinders the penetration rate in most cases. Therefore, the present invention does not need to add any transdermal enhancer.

Example 22

A multi-layer transdermal drug delivery system containing ibuprofen comprises a transdermal patch containing ibuprofen (referred to as a first combined layer for short) and a second combined layer. The second combined layer comprises a backing layer, a protective layer, and a polymer matrix layer located between the backing layer and the protective layer. The transdermal patch containing ibuprofen (i.e., the first combined layer) can be optionally selected from the transdermal patch containing ibuprofen in Examples 1-21.

The polymer matrix layer of the second combined layer comprises a pressure-sensitive adhesive and a pharmaceutically acceptable auxiliary material, and may also comprise active ingredients such as ibuprofen. When the polymer matrix layer of the second combined layer contains ibuprofen, the content by weight of ibuprofen is ≤15%, for example, ≤10%, ≤8%, or ≤5%.

The second combined layer can be prepared by referring to the preparation method of the transdermal patch containing ibuprofen in Example 1.

The formulations of the polymer matrix layer of a typical second combined layer (i.e., Examples 22-26) were shown in Table 3.

TABLE 3

(Table 3 shows the percentage by weight.)

| Example | Ibuprofen | Duro-tack-2074 | Duro-tack-4098 | Duro-tack-6908 | Bio-PSA 7-4302 | BHA |
|---|---|---|---|---|---|---|
| 22 | 5 | 94 | | | | 1 |
| 23 | 1 | | 98 | | | 1 |
| 24 | 2 | | | 97 | | 1 |
| 25 | 0 | | | | 100 | |
| 26 | 1 | 49 | | | 49 | 1 |

Example 27

Figure 6:
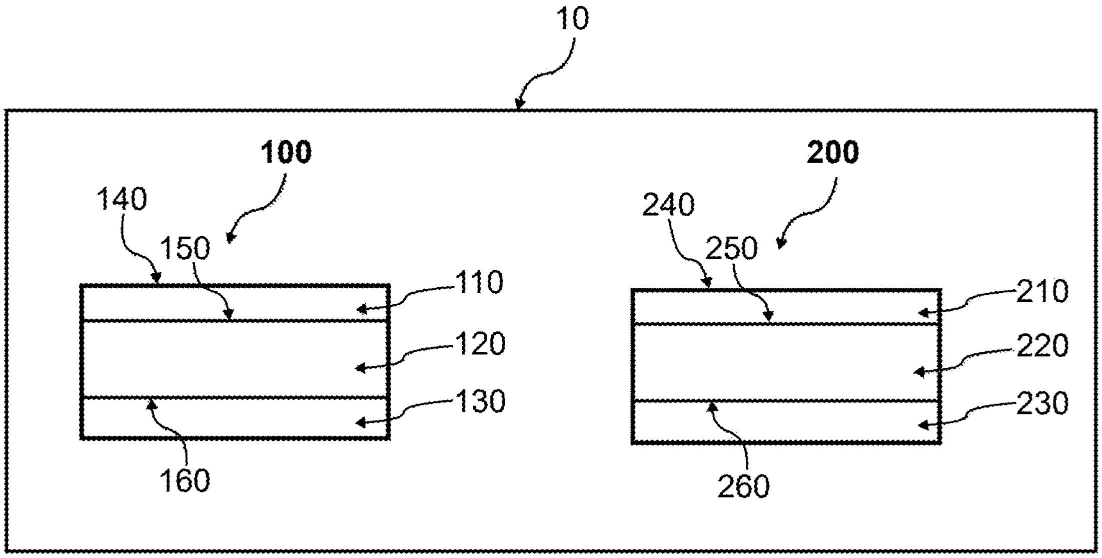
FIG. 6 shows the schematic diagram of the structure of the transdermal patch containing ibuprofen (FIG. 6A) and the schematic diagram of the structure of the second combined layer (FIG. 6B) of the present invention.

A schematic diagram of the structure of the transdermal patch containing ibuprofen in Example 1 is shown in FIG. 6A. A schematic diagram of the structure of the second combined layer in Example 22 is shown in FIG. 6B. The two constitute a multi-layer transdermal drug delivery system 10 containing ibuprofen.

The transdermal patch 100 containing ibuprofen and the second combined layer 200 are separate before use, and each comprises a backing layer, a protective layer, and a polymer matrix layer located between the backing layer and the protective layer.

For the transdermal patch 100 containing ibuprofen, the inner side 150 of the backing layer 110 is directly attached to one side of the polymer matrix layer 120, and the other side 140 of the backing layer 110 is exposed to the environment to protect the polymer matrix layer 120. The inner side 160 of the protective layer 130 is attached to the other side of the polymer matrix layer 120, and the polymer matrix layer 120 is located between the protective layer 130 and the backing layer 110 before use.

For the second combined layer 200, the inner side 250 of the backing layer 210 is directly attached to one side of the polymer matrix layer 220, and the other side 240 of the backing layer 210 is exposed to the environment to protect the polymer matrix layer 220. The inner side 260 of the protective layer 230 is attached to the other side of the polymer matrix layer 220, and the polymer matrix layer 220 is located between the protective layer 210 and the backing layer 230 before use.

When using, the protective layer 130 in the transdermal patch 100 containing ibuprofen is first removed, and the transdermal patch 100 is applied to the patient's skin. Then the protective layer 230 of the second combined layer 200 is removed, and the second combined layer 200 is completely covered on the first combined layer 100, so that the first combined layer 100 is completely covered by the second combined layer 200. The second combined layer is 0.5 to 1.0 cm wider than the periphery of the transdermal patch containing ibuprofen.

Experimental Example 1

Stability Experiment

The patches of Comparative Example 1 and Example 1 were stored under the same storage conditions (30±2° C., 60%±10% RH), and observed regularly by an electron microscope. The observation results were shown in FIG. 1.

The results of continuous observation showed that in the absence of amino compounds, the active ingredient was precipitated from the polymer matrix in the first week, and obvious crystals could be observed. In Example 1, there was no change during the twelve-month observation period, ibuprofen was uniformly dispersed in the adhesive matrix, no crystals were found under different magnifications of an optical microscope, and no crystallization phenomenon was observed, indicating that the patch had good stability.

Experimental Example 2

In Vitro Release Experiment

In vitro release is a basic performance index of the patch, which reflects the interaction between the active ingredient and other components in the polymer matrix. The overall properties of the polymer matrix, the interactions between ibuprofen and the polymer and other components, such as hydrogen bonds, ion pairs, and van der Waals forces, lead to different flow behaviors of ibuprofen in the polymer matrix. In vitro release is the basis of transdermal absorption, and only suitable release capacity can meet the specific requirements of transdermal absorption.

A release test (Chinese Pharmacopoeia, 2015 edition, Volume IV, general principle 0931, Fourth method-paddle over disk) was used to operate with PBS as a dissolution medium, at a temperature of 32° C. and 50 revolutions/min, and a sample of 10 ml was taken at 0.3 h, 0.5 h, 0.7 h, 1.0 h, 1.5 h, 2.0 h, 3.0 h, 6.0 h, 9.0 h, 12.0 h, 18.0 h and 24.0 h, respectively, and filtered. In addition, an appropriate amount of ibuprofen reference substance was accurately weighed and dissolved with the dissolution medium, to prepare a solution of appropriate concentration as a reference solution.

With octadecyl silane bonded silica gel as a filler, a methanol-phosphate aqueous solution (40 mmol/L potassium dihydrogen phosphate aqueous solution, phosphoric acid was used to adjust pH to 2.50) (77:23) as a mobile phase, a detection wavelength of 225 nm, a column temperature of 50° C., and the number of theoretical plates not less than 2,000 calculated by ibuprofen, determination was performed according to HPLC method (Chinese Pharmacopoeia, 2015 edition, Volume IV, general principle 0512).

Figure 2:
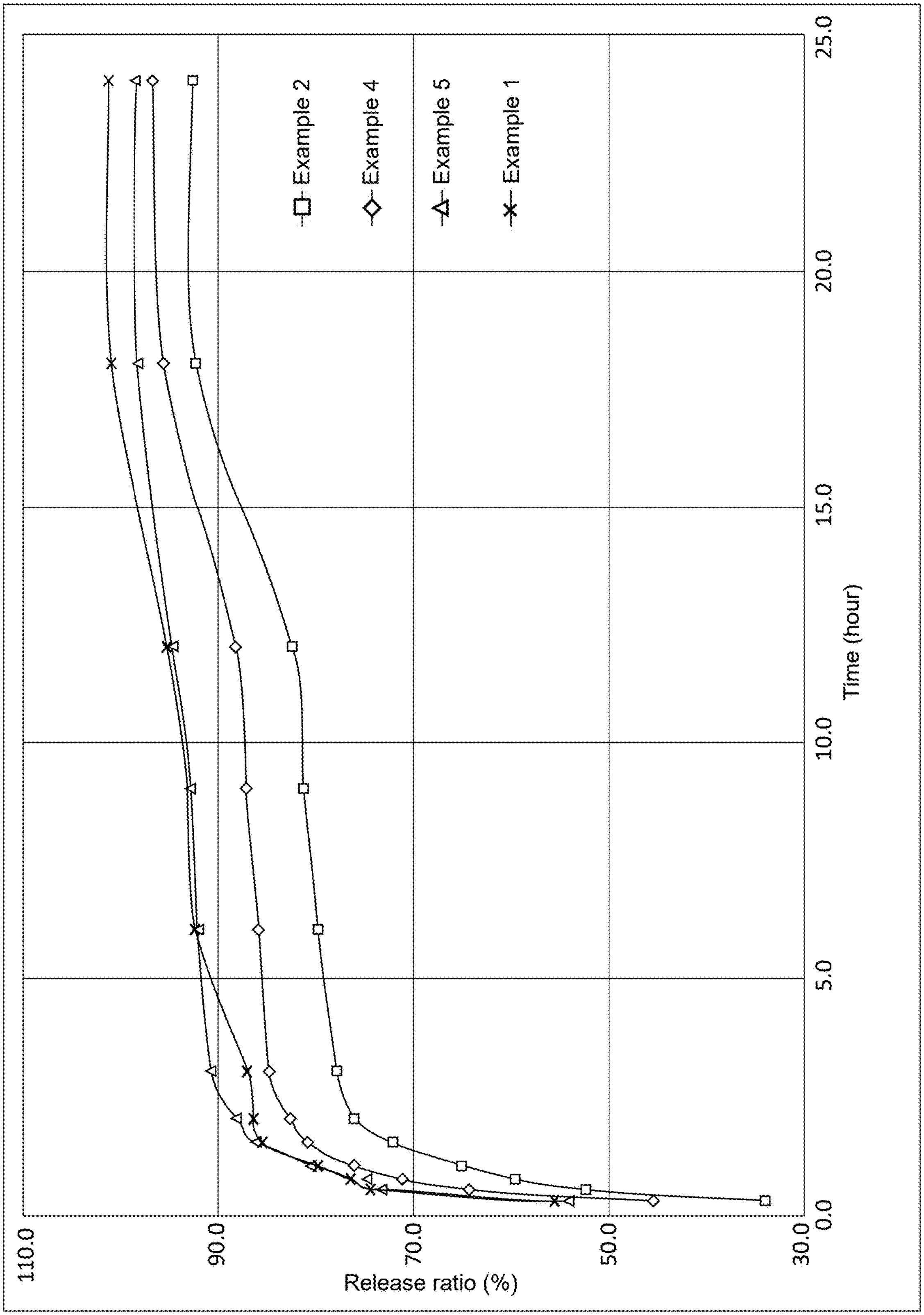
FIG. 2 shows the results of the in vitro release experiment of Experimental Example 2.

The results were shown in FIG. 2. The results show that Examples 1, 2, 4, and 5 all have relatively fast release behavior, and the release is basically complete in the first 2 hours. The release behavior fully meets the requirements of transdermal absorption and will not hinder the overall transdermal absorption behavior.

Experimental Example 3

In Vitro Transdermal Experiment

The in vitro transdermal experiment was measured by a Franz vertical diffusion cell. The cuticle of the skin of the healthy adult pig ear was obtained according to the standard heat separation method. The receiving solution was a PBS solution with a pH of 7.4, the receiving cell had a volume of 7 mL, the temperature was set at 32±0.1° C., and the stirring speed was 300 revolutions/minute. Samples were taken at 1 h, 2 h, 3 h, 4 h, 5 h, 6 h, 8 h, 10 h, 12 h and 24 h, respectively, each sample was of a volume of 3 mL, and then an isothermal blank receiving solution was added. Each group of samples were subjected to parallel experiment for 6 times, and meanwhile, a placebo parallel experiment was used as a control. The cumulative penetration amount at each time point was calculated based on the results.

Figure 3:
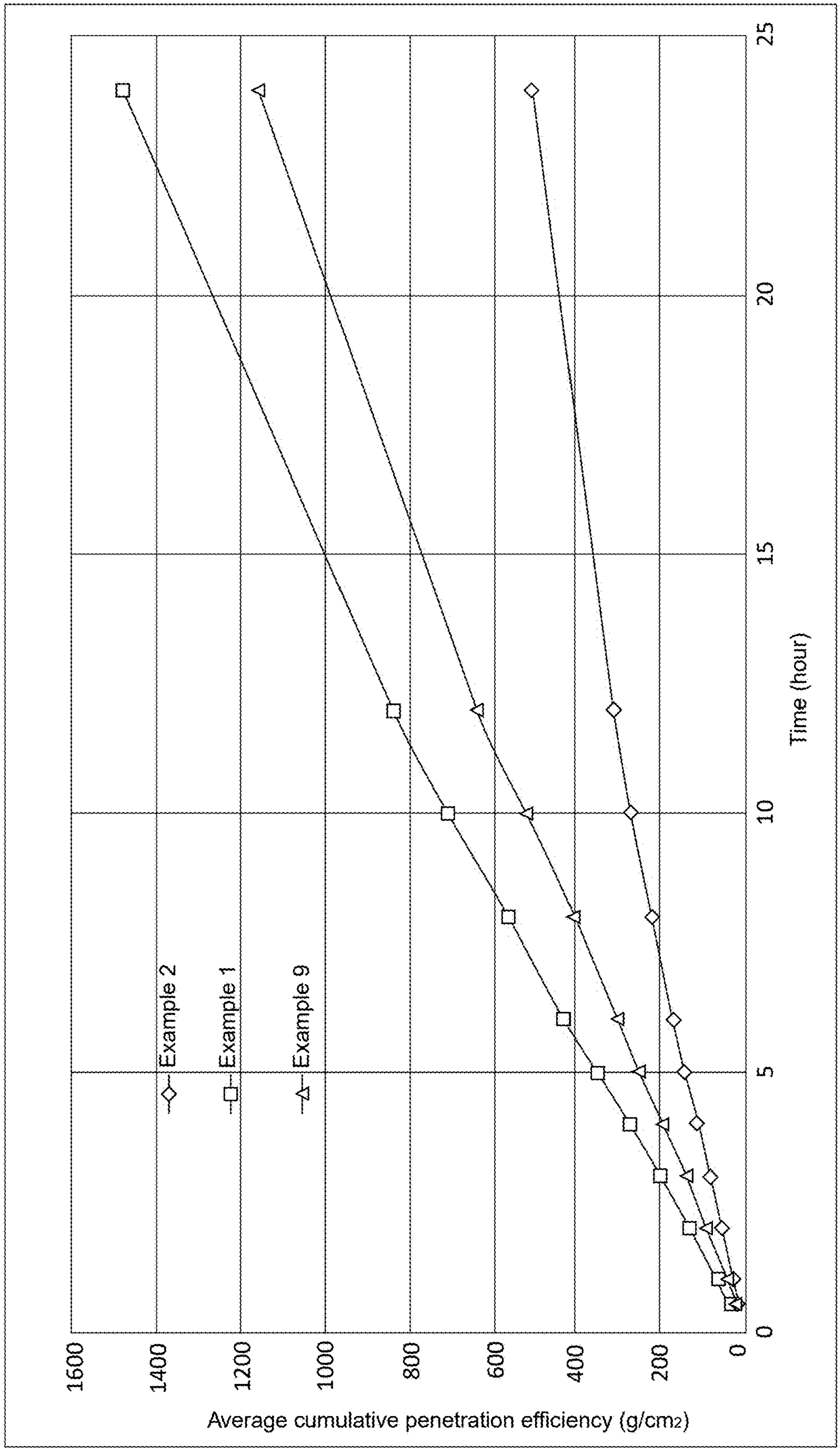
FIG. 3 shows the results of the in vitro transdermal experiment of Experimental Example 3.

The results were shown in FIG. 3. The results show that within the 24-hour experimental range, the patch of the present invention can regulate the release rate and the total release amount, so as to deliver an amount of ibuprofen with therapeutic effect according to the need of use.

Experimental Example 4

Human Blood Drug Concentration Experiment in Healthy Volunteers

Twelve healthy adult males, aged 24.6±2.5 (22 to 30) years old, and weighing 61.2±2.8 (58 to 65) kg were selected. The subjects had no history of drug allergy and had not used any drugs in the past two weeks. During the experiment, other drugs were forbidden, and the diet was uniform during the test period. Fenbid® was selected as the control drug (400 mg/ibuprofen sustained-release capsule, batch number: 17090198), and the subject took one capsule orally. The transdermal patches of Examples 3 and 6 were selected, and applied to the lower part of the abdomen of each subject. The 12 subjects were randomly divided into three groups, with 4 people in each group. Fenbid® was taken orally in the first group, the transdermal patch of Example 3 was applied in the second group, and the transdermal patch of Example 6 was applied in the third group.

Blood sampling method: blood was taken from upper limb vein at 0 h, 0.25 h, 0.5 h, 1 h, 2 h, 3 h, 6 h, 9 h, 12 h, 15 h, 18 h, and 24 h, respectively, with a blood volume of 5 mL each time.

Detection Method: HPLC Method; Chromatographic Conditions:

Chromatographic column: C18; 150*4.6 mm; 5 μm; mobile phase: 5.4 g/L potassium dihydrogen phosphate aqueous solution (pH=2.50, adjusted by phosphoric acid): methanol=30:70; column temperature: 50° C.; flow rate: 1.0 mL/min; detection wavelength: 225 nm; injection volume: 20 μl; elution mode: equal concentration elution; and injection mode: automatic injection.

Sample processing method: protein precipitation method (0.2 ml of serum was added to 0.2 ml of acetonitrile, vortexing was performed to mix evenly, centrifugation was performed at 10,000 r/min for 15 min, and the supernatant was taken).

Figure 4:
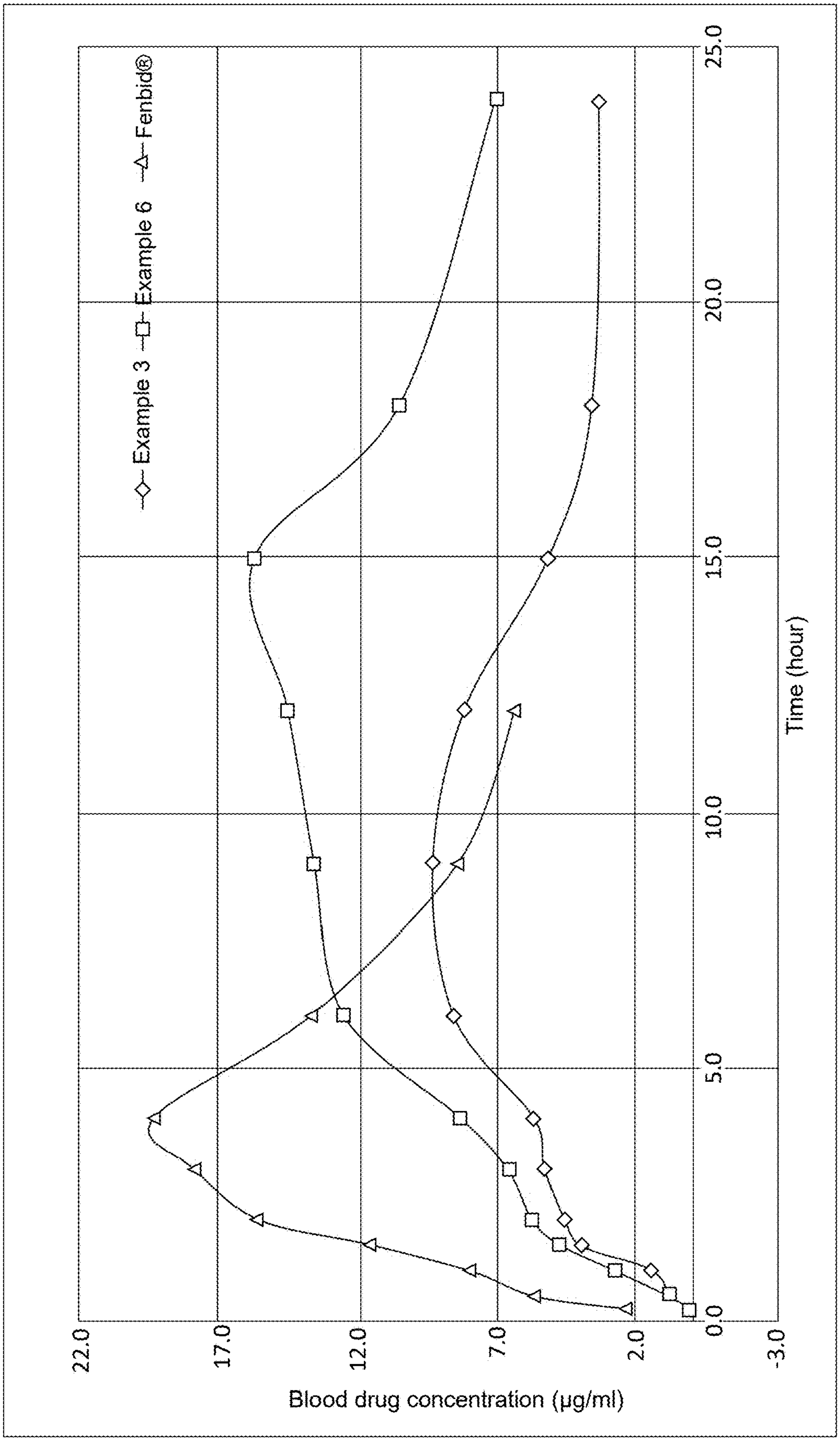
FIG. 4 shows the results of the human blood drug concentration experiment of Experimental Example 4.

The specific results were shown in FIG. 4. The results show that compared with Fenbid® sustained-release capsules, the patch of the present invention can continuously increase the blood drug concentration within 8 hours, and then the blood drug concentration will steadily decrease in the following 4 hours, achieving a stable clinical effect for 12 hours. Meanwhile, the blood drug concentration can continue to increase within 15 hours, and then decrease steadily in the following 8 hours, achieving a stable clinical effect for 24 hours. Therefore, the patch of the present invention can deliver a therapeutically effective dose of ibuprofen within 12 to 24 hours according to the requirements of the therapeutic effect.

Experimental Example 5

Fever Inducing-Fever Reducing Experiment in Rats

Animals: Wistar rats, males, weighing 300 g±20 g, were divided into 5 groups (four rats in each group). One group was subjected to the application of the patch of Example 1, three groups were used to receive different doses of Merlin™ (5 mg, 10 mg and 20 mg, respectively) by gavage, and one group was used as a blank control after fever inducing.

Fever inducing method: subcutaneous injection of dry yeast solution at the back of the neck (4 ml of 30% dry yeast solution per 300 g was injected).

Temperature measurement method: 3 cm depth of the anus, electronic thermometer, the average value of two parallel measurements was taken (the deviation of the two measurement results was no more than ±0.1° C.).

Shaving method: After anesthesia, most of the hair was removed with an electric shaver, and then the rats were evenly applied with a depilatory cream, and rinsed with water after 3 minutes.

Mode of Administration:

In the patch group, the patch of Example 1 was applied to the abdomen of the rat and fixed with gauze.

| Information about Example 1 | |
|---|---|
| Patch area | 15 $cm^2$ |
| Active ingredient content % | 35 |
| Drug loading $mg/cm^2$ | 2.6 |

In the oral group, each group of animals were given 5 mg, 10 mg, and 20 mg of Merlin™ (Johnson & Johnson, concentration of 20 mg/ml; production batch number: 171101428) by gavage.

Figure 5:
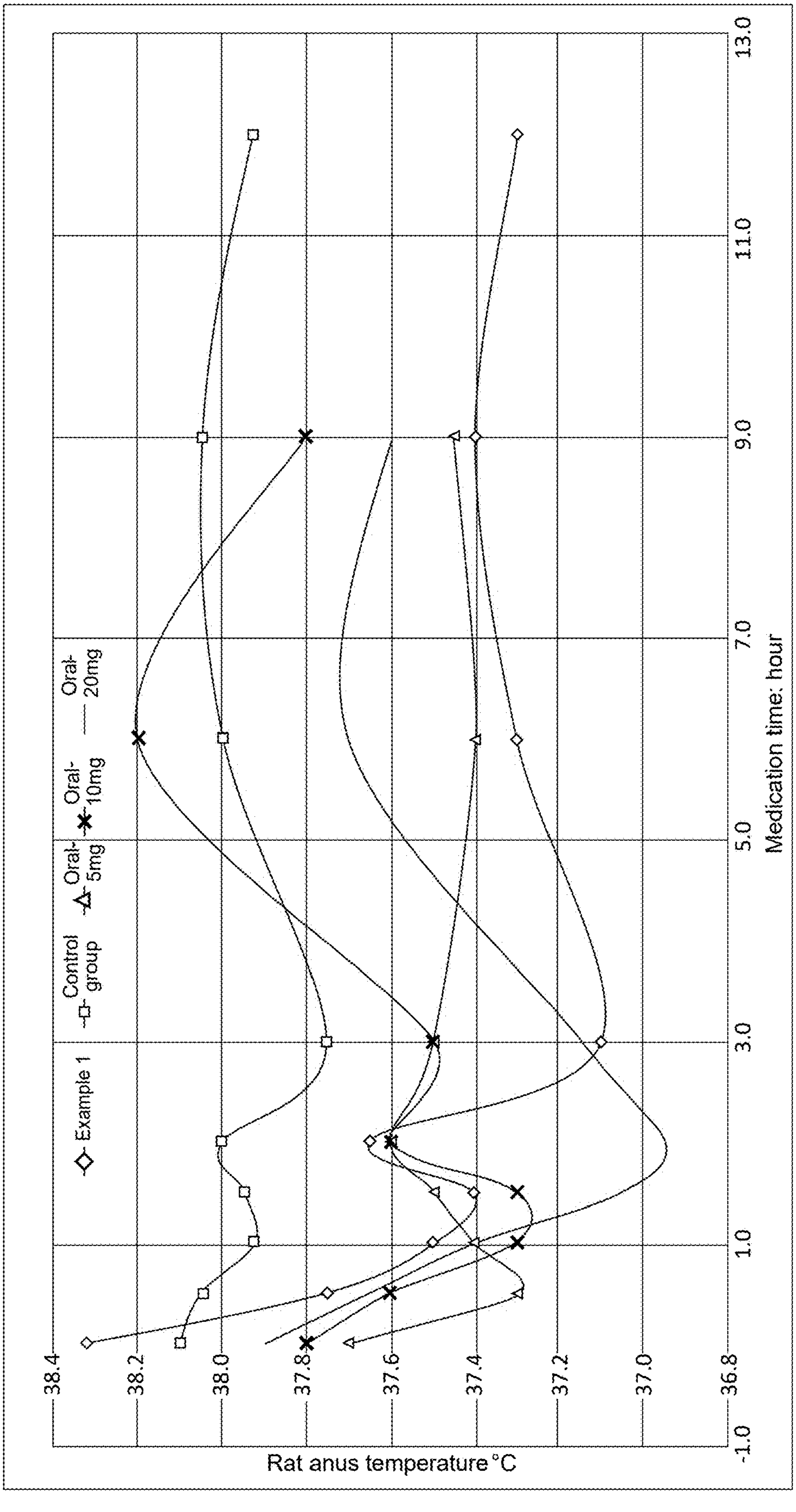
FIG. 5 shows the results of fever inducing-fever reducing experiment in rats of Experimental Example 5.

The specific results were shown in FIG. 5. The results show that, compared with the relatively short antipyretic effect of oral Merlin™, the patch of the present invention has a stable antipyretic effect for a long time, and the antipyretic effect is stable with a long duration.

Experimental Example 6

Application Experiment

Healthy adult subjects were selected, the application site was on the inner side of the upper arm, and the residues on skin and cold flow phenomenon were investigated.

The experimental grouping was as follows:

1) The transdermal patches containing ibuprofen of Examples 2, 4, and 6 were used separately. Method was as follows: firstly, the protective layer was removed, and then the patch was applied to the inner side of the volunteer's upper arm.

2) The second combined layer (the matrix formulation was the same as that of Example 22) was used separately. Method was as follows: firstly, the protective layer was removed, and then the second combined layer was applied to the inner side of the volunteer's upper arm.

3) A multi-layer transdermal drug delivery system containing ibuprofen was used: the transdermal patches containing ibuprofen of Examples 2, 4, and 6 were respectively used as the first combined layer, in combination with the second combined layer (the matrix formulation was the same as that of Example 22). Combination use method was as follows: the protective layer of the second combined layer was removed, the second combined layer was applied to the backing layer of the transdermal patches of Examples 2, 4, and 6 as the first combined layers, respectively, and then the protective layer of the transdermal patch was removed to apply the transdermal patch to the inner side of the upper arm.

In the above groups, the patches were removed at 4 h, 8 h, 12 h and 24 h, respectively, and the residual and the degree of cold flow at the application site were observed. The observation results were shown in Table 4.

TABLE 4

| | | Application time: 4 h | | Application time: 8 h | | Application time: 12 h | | Application time: 24 h | |
|---|---|---|---|---|---|---|---|---|---|
| Example | Application site | Residual degree | Cold flow degree | Residual degree | Cold flow degree | Residual degree | Cold flow degree | Residual degree | Cold flow degree |
| 2 | Inner side of upper arm | C | C | C | B | C | B | C | B |
| 4 | Inner side of upper arm | C | C | C | B | C | A | C | A |
| 6 | Inner side of upper arm | C | B | B | B | B | A | B | A |
| 22 | Inner side of upper arm | C | C | C | C | C | C | C | C |
| Combination 2 + 22 | Inner side of upper arm | C | C | C | C | C | C | C | C |
| Combination 4 + 22 | Inner side of upper arm | C | C | C | C | C | C | C | C |
| Combination 6 + 22 | Inner side of upper arm | C | C | C | C | C | C | C | B |

A = obvious;
B = slight;
C = none

From the observation results, it can be seen that the patch of the present invention basically has no residues. In the absence of the second combined layer, an obvious cold flow phenomenon was observed, as shown in Example 4 and Example 6, but in the case of using the combination, the cold flow phenomenon was eliminated.

The above relevant experiments were carried out using ibuprofen as the active ingredient. Due to the similar structures, properties and functions, a person skilled in the art can foresee the structural analogues of ibuprofen: naproxen, fenoprofen, ketoprofen, flurbiprofen, and loxoprofen, can also achieve basically the same functions and achieve basically the same technical correlations. Due to space limitations, the relevant experiments could not be listed.

Although the present invention has been described in detail above with general descriptions and specific embodiments, some modifications or improvements can be made on the basis of the present invention, which is obvious to a person skilled in the art. Therefore, these modifications or improvements made without departing from the spirit of the present invention belong to the scope of the present invention.

INDUSTRIAL APPLICABILITY

The present invention provides a multi-layer transdermal drug delivery system containing ibuprofen or a structural analogue thereof. The multi-layer transdermal drug delivery system comprises a transdermal patch containing ibuprofen or a structural analogue thereof and a second combined layer. The transdermal patch comprises a polymer matrix layer comprising an active ingredient, a compound containing at least one amino group, and a pressure-sensitive adhesive. All or part of the active ingredient-amino compound salts and all or part of free active ingredient formed in the polymer matrix layer are kept in a uniform dissolution state in the polymer matrix, and can be stably stored before use, without recrystallization. The present invention also provides the preparation method and the use method of the transdermal drug delivery system. The transdermal drug delivery system of the present invention can continuously and controllably deliver a therapeutically effective dose of ibuprofen or its structural analogue in the range of 12 to 24 hours without a transdermal enhancer. The transdermal drug delivery system of the present invention has excellent wearability, avoids a cold flow phenomenon, and has good economic value and application prospects.

What is claimed is:

1. A transdermal patch containing ibuprofen, wherein the transdermal patch comprises a polymer matrix layer comprising:

an active ingredient, a compound containing at least one amino group, wherein the compound containing at least one amino group is an unprotonated fatty amine, a pressure-sensitive adhesive, and a filler in an amount of from 0.5% to 10% by weight of the total dry polymer matrix, wherein the filler comprises colloidal silicon dioxide;

wherein the active ingredient is ibuprofen;

wherein in the polymer matrix layer, part of the active ingredient forms a salt with the unprotonated fatty amine; a molar ratio of the active ingredient in the polymer matrix layer to the amino group in the compound containing at least one amino group is 12:1 to 1:1; and a content by weight of the active ingredient in the polymer matrix layer is 15% to 45%.

2. The transdermal patch according to claim 1, wherein the fatty amine comprises one or more of ethanolamine, diethanolamine, triethanolamine, diethylamine, triethylamine, propane diamine, N-ethylmorpholine, N-ethylpiperidine, N-ethylpiperazine, N-hydroxyethylpiperidine, N-hydroxyethylpyrrole, dimethylpropanediamine, tetramethylpropanediamine, N-dodecylpyrrole, trihexylamine, N-dodecyl homopiperidine, pyridin-2-yl-methanol, ethylenediamine, tetramethyl ethylenediamine, spermidine, spermine, cyclen, 3-(piperazin-1-yl) propan-1,2-diol, N-hydroxyethylpiperazine, N-methylmorpholine, triethylenediamine, tris(2-aminoethyl)amine, 2-piperazinone, 3-aminopiperidine, 1,3-cyclohexanedimethylamine, propylene glycol bis(3-aminopropyl) ether, and ethylene glycol bis(3-aminoethyl) ether.

3. The transdermal patch according to claim 2, wherein the melting point of the formed active ingredient-amino compound salt is lower than the melting point of ibuprofen.

4. The transdermal patch according to claim 2, wherein a surface area of the filler ranges from 1.5 $m^2/g$ to 15 $m^2/g$.

5. The transdermal patch according to claim 2, wherein the polymer matrix layer does not contain a transdermal enhancer, wherein the transdermal enhancer is selected from the group consisting of propylene glycol, PEG600, olive oil, squalene, silicone oil, mineral oil, oleic acid, isopropyl myristate, cetyl palmitate, propylene glycol monocaprylate, caprylic/capric triglyceride, ethyl oleate, oleoyl polyoxyl-6 glyceride, urea, azone, N-methylpyrrolidone, dimethyl sulfoxide and glycerin.

6. The transdermal patch according to claim 2, wherein a molar ratio of the active ingredient in the polymer matrix layer to the amino group in the compound containing at least one amino group is 10:1 to 1.5:1; and/or, a content by weight of the compound containing at least one amino group in the polymer matrix layer is 1% to 15%; and/or, a content by weight of the active ingredient in the polymer matrix layer is 20% to 40%; and/or a content by weight of the pressure-sensitive adhesive in the polymer matrix layer is 40% to 80%.

7. The transdermal patch according to claim 2, wherein the patch further comprises a backing layer and a protective layer; and the polymer matrix layer is located between the backing layer and the protective layer.

8. The transdermal patch according to claim 1, wherein the melting point of the formed active ingredient-amino compound salt is lower than the melting point of ibuprofen.

9. The transdermal patch according to claim 8, wherein a surface area of the filler ranges from 1.5 $m^2/g$ to 15 $m^2/g$.

10. The transdermal patch according to claim 8, wherein the polymer matrix layer does not contain a transdermal enhancer.

11. The transdermal patch according to claim 8, wherein a molar ratio of the active ingredient in the polymer matrix layer to the amino group in the compound containing at least one amino group is 10:1 to 1.5:1; and/or, a content by weight of the compound containing at least one amino group in the polymer matrix layer is 1% to 15%; and/or, a content by weight of the active ingredient in the polymer matrix layer is 20% to 40%; and/or, a content by weight of the pressure-sensitive adhesive in the polymer matrix layer is 40% to 80%.

12. The transdermal patch according to claim 1, wherein a surface area of the filler ranges from 1.5 $m^2/g$ to 15 $m^2/g$.

13. The transdermal patch according to claim 12, wherein the polymer matrix layer does not contain a transdermal enhancer.

14. The transdermal patch according to claim 1, wherein the polymer matrix layer does not contain a transdermal enhancer.

15. The transdermal patch according to claim 1, wherein a molar ratio of the active ingredient in the polymer matrix layer to the amino group in the compound containing at least one amino group is 10:1 to 1.5:1; and/or, a content by weight of the compound containing at least one amino group in the polymer matrix layer is 1% to 15%; and/or, a content by weight of the active ingredient in the polymer matrix layer is 20% to 40%; and/or, a content by weight of the pressure-sensitive adhesive in the polymer matrix layer is 40% to 80%.

16. The transdermal patch according to claim 1, wherein the patch further comprises a backing layer and a protective layer; and the polymer matrix layer is located between the backing layer and the protective layer.

17. A multi-layer transdermal drug delivery system containing ibuprofen, wherein the multi-layer transdermal drug delivery system comprises the transdermal patch according to claim 1, and further comprises a second combined layer; the second combined layer comprises a backing layer, a protective layer, and a polymer matrix layer located between the backing layer and the protective layer; and the polymer matrix layer comprises a pressure-sensitive adhesive.

18. The multi-layer transdermal drug delivery system according to claim 17, wherein the polymer matrix layer of the second combined layer further comprises a pharmaceutically acceptable auxiliary material, and/or further comprises ibuprofen; and a content by weight of ibuprofen in the polymer matrix layer of the second combined layer is ≤15%.

19. The multi-layer transdermal drug delivery system according to claim 18, wherein a peripheral width of the second combined layer is 0.5 cm to 1.0 cm wider than the peripheral width of the transdermal patch.

20. The multi-layer transdermal drug delivery system according to claim 17, wherein a peripheral width of the second combined layer is 0.5 cm to 1.0 cm wider than the peripheral width of the transdermal patch.

* * * * *